(12) United States Patent
Farmer et al.

(10) Patent No.: US 12,048,463 B2
(45) Date of Patent: Jul. 30, 2024

(54) EXTENDED TAB REINFORCEMENT SLEEVE

(71) Applicant: Zimmer Biomet Spine, Inc., Westminster, CO (US)

(72) Inventors: Heidi Farmer, Lafayette, CO (US); Jared Parker, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

(21) Appl. No.: 18/158,279

(22) Filed: Jan. 23, 2023

(65) Prior Publication Data

US 2023/0157735 A1     May 25, 2023

Related U.S. Application Data

(63) Continuation of application No. 16/693,733, filed on Nov. 25, 2019, now Pat. No. 11,559,337.

(60) Provisional application No. 62/779,905, filed on Dec. 14, 2018.

(51) Int. Cl.
*A61B 17/70*     (2006.01)
*A61B 17/86*     (2006.01)
*A61B 17/00*     (2006.01)
*A61B 90/00*     (2016.01)

(52) U.S. Cl.
CPC ........ *A61B 17/708* (2013.01); *A61B 17/7001* (2013.01); *A61B 17/862* (2013.01); *A61B 17/00234* (2013.01); *A61B 2017/00349* (2013.01); *A61B 2017/00367* (2013.01); *A61B 2017/00862* (2013.01); *A61B 17/7082* (2013.01); *A61B 2017/8655* (2013.01); *A61B 2090/037* (2016.02)

(58) Field of Classification Search
CPC ............ A61B 17/7077; A61B 17/7079; A61B 17/7085; A61B 17/708
See application file for complete search history.

(56) References Cited

U.S. PATENT DOCUMENTS

| | | | |
|---|---|---|---|
| 7,179,261 B2 * | 2/2007 | Sicvol | A61B 17/8605 606/86 A |
| 7,612,918 B2 * | 11/2009 | Suzuki | H04N 1/409 358/463 |
| 8,211,110 B1 | 7/2012 | Corin et al. | |
| 8,439,922 B1 | 5/2013 | Arnold et al. | |
| 8,603,094 B2 | 12/2013 | Walker et al. | |

(Continued)

FOREIGN PATENT DOCUMENTS

WO    WO 2014/144274 A1    9/2014

OTHER PUBLICATIONS

Sloan, Robert, "CD Horizon Voyager, Mini-Open Rod System, Surgical Technique", Medtronic, (2012), 36 pages.

(Continued)

*Primary Examiner* — Matthew J Lawson
(74) *Attorney, Agent, or Firm* — Sheridan Ross P.C.

(57) ABSTRACT

A sleeve can be adapted to reinforce a bone anchor, and can include a body, a lock, and an actuator. The body can include a first sleeve arm and a second sleeve arm, where each can extend longitudinally along opposing sides of a longitudinal bore open at a distal end of the sleeve. The lock can be coupled to the body and releasably securable to a channel of a head of the bone anchor to secure the sleeve to the anchor.

19 Claims, 21 Drawing Sheets

(56) References Cited

U.S. PATENT DOCUMENTS

| | | | |
|---|---|---|---|
| 9,192,415 B1 | 11/2015 | Arnold et al. | |
| 9,198,698 B1* | 12/2015 | Doose | A61B 17/7001 |
| 9,211,149 B2 | 12/2015 | Hoefer et al. | |
| 9,220,543 B2 | 12/2015 | Walker et al. | |
| 9,333,012 B2 | 5/2016 | Beale et al. | |
| 9,370,383 B2 | 6/2016 | Parker et al. | |
| 9,492,209 B2 | 11/2016 | Biedermann et al. | |
| 9,629,661 B2 | 4/2017 | Kraus | |
| 9,907,582 B1* | 3/2018 | Olea | A61B 17/7086 |
| 9,924,982 B2 | 3/2018 | Jackson | |
| 9,980,758 B2 | 5/2018 | Abidin | |
| 10,245,082 B2 | 4/2019 | Parker et al. | |
| 10,299,839 B2 | 5/2019 | Sicvoi et al. | |
| 10,398,481 B2 | 9/2019 | Goel et al. | |
| 10,426,527 B2 | 10/2019 | Doose et al. | |
| 10,485,588 B2 | 11/2019 | Jackson | |
| 10,631,901 B2* | 4/2020 | Fiechter | A61B 17/8891 |
| 11,439,441 B2* | 9/2022 | Mickiewicz | A61B 17/0206 |
| 11,559,337 B2 | 1/2023 | Farmer et al. | |
| 2002/0116006 A1 | 8/2002 | Cohen et al. | |
| 2005/0131408 A1* | 6/2005 | Sicvol | A61B 17/708 |
| | | | 606/301 |
| 2006/0074418 A1 | 4/2006 | Jackson | |
| 2006/0079894 A1 | 4/2006 | Colleran et al. | |
| 2006/0079909 A1 | 4/2006 | Runco et al. | |
| 2007/0233079 A1 | 10/2007 | Fallin et al. | |
| 2008/0077134 A1 | 3/2008 | Dziedzic et al. | |
| 2009/0143828 A1 | 6/2009 | Stad et al. | |
| 2009/0149892 A1 | 6/2009 | Stad et al. | |
| 2011/0034962 A1 | 2/2011 | Dunbar et al. | |
| 2011/0313463 A1 | 12/2011 | Mclean | |
| 2012/0022594 A1 | 1/2012 | Walker et al. | |
| 2012/0035668 A1 | 2/2012 | Manninen et al. | |
| 2012/0116460 A1 | 5/2012 | Gorek | |
| 2013/0245702 A1 | 9/2013 | Mcbride | |
| 2013/0245705 A1 | 9/2013 | Mcbride et al. | |
| 2013/0261679 A1 | 10/2013 | Mcbride et al. | |
| 2014/0039567 A1 | 2/2014 | Hoefer et al. | |
| 2014/0052187 A1* | 2/2014 | McBride | A61B 17/7085 |
| | | | 606/264 |
| 2014/0148865 A1 | 5/2014 | Hennard et al. | |
| 2014/0163625 A1 | 6/2014 | Meyer et al. | |
| 2014/0276895 A1 | 9/2014 | Jackson et al. | |
| 2014/0277200 A1 | 9/2014 | Parker et al. | |
| 2014/0277206 A1 | 9/2014 | Reitblat et al. | |
| 2014/0316475 A1 | 10/2014 | Parikh et al. | |
| 2015/0039035 A1 | 2/2015 | Kruger | |
| 2015/0051648 A1 | 2/2015 | May et al. | |
| 2015/0066042 A1 | 3/2015 | Cummins et al. | |
| 2015/0073485 A1 | 3/2015 | Butler et al. | |
| 2015/0112397 A1* | 4/2015 | Petit | A61B 17/7082 |
| | | | 606/86 A |
| 2015/0359571 A1 | 12/2015 | Biedermann et al. | |
| 2016/0113682 A1 | 4/2016 | Altarac et al. | |
| 2016/0338744 A1 | 11/2016 | Parker et al. | |
| 2017/0079696 A1 | 3/2017 | Walker et al. | |
| 2017/0164980 A1* | 6/2017 | Le Roux | A61B 17/7032 |
| 2017/0164985 A1 | 6/2017 | Reitblat et al. | |
| 2018/0008318 A1* | 1/2018 | Fiechter | A61B 17/8891 |
| 2018/0042645 A1 | 2/2018 | Gunn et al. | |
| 2019/0223924 A1 | 7/2019 | Parker et al. | |
| 2020/0197052 A1 | 6/2020 | Huer et al. | |

OTHER PUBLICATIONS

Notice of Allowance for Canadian Patent Application No. 3065039, dated Jan. 4, 2022 1 page.

"European Application Serial No. 19215706.3, Extended European Search Report mailed May 12, 2020", 9 pages.

Official Action for U.S. Appl. No. 16/693,733, dated Feb. 14, 2022 14 pages.

Final Action for U.S. Appl. No. 16/693,733, dated Jun. 22, 2022 7 pages.

Notice of Allowance for U.S. Appl. No. 16/693,733, dated Sep. 8, 2022 5 pages.

Official Action for European Patent Application No. 19215706.3, dated Sep. 27, 2023 7 pages.

* cited by examiner

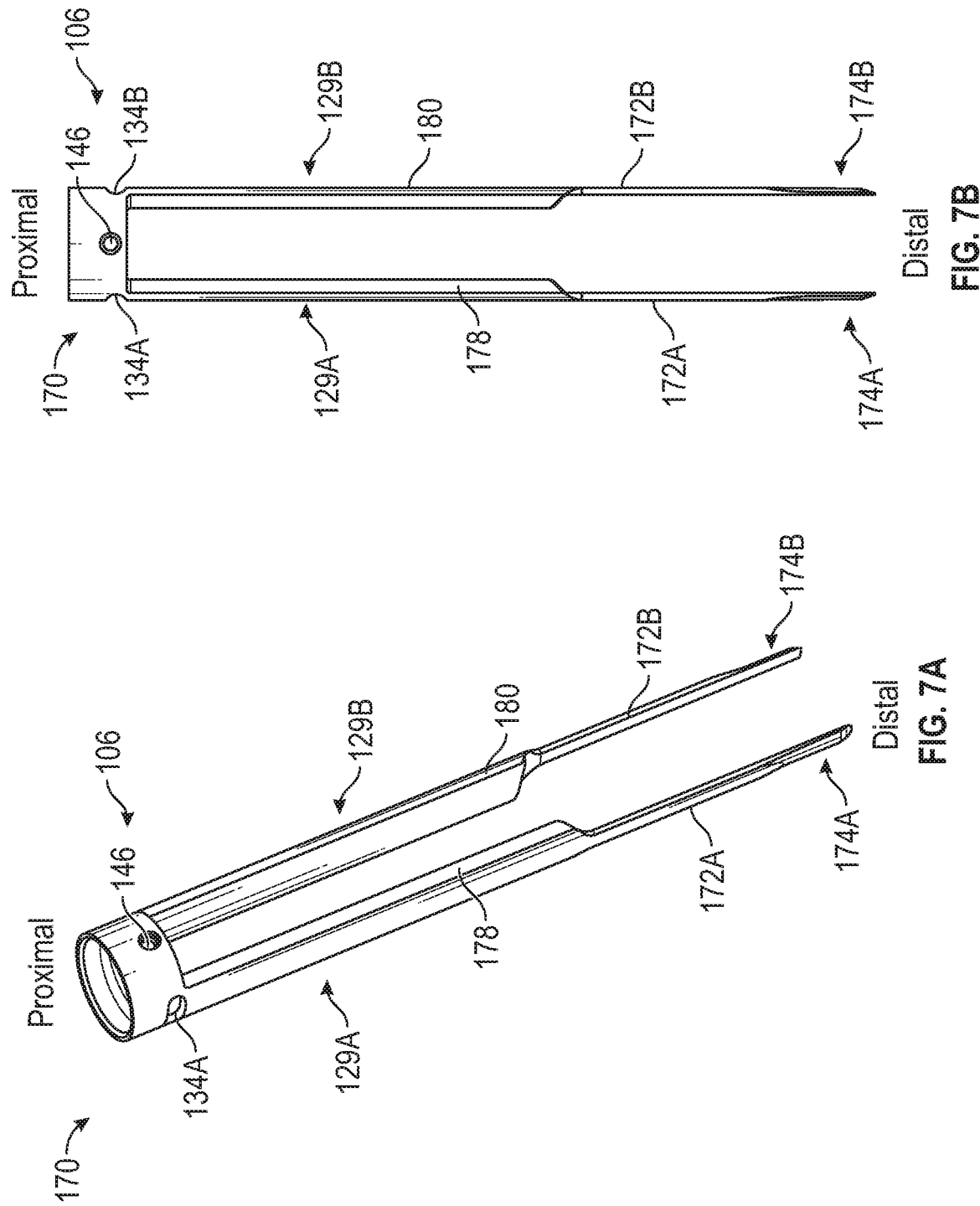

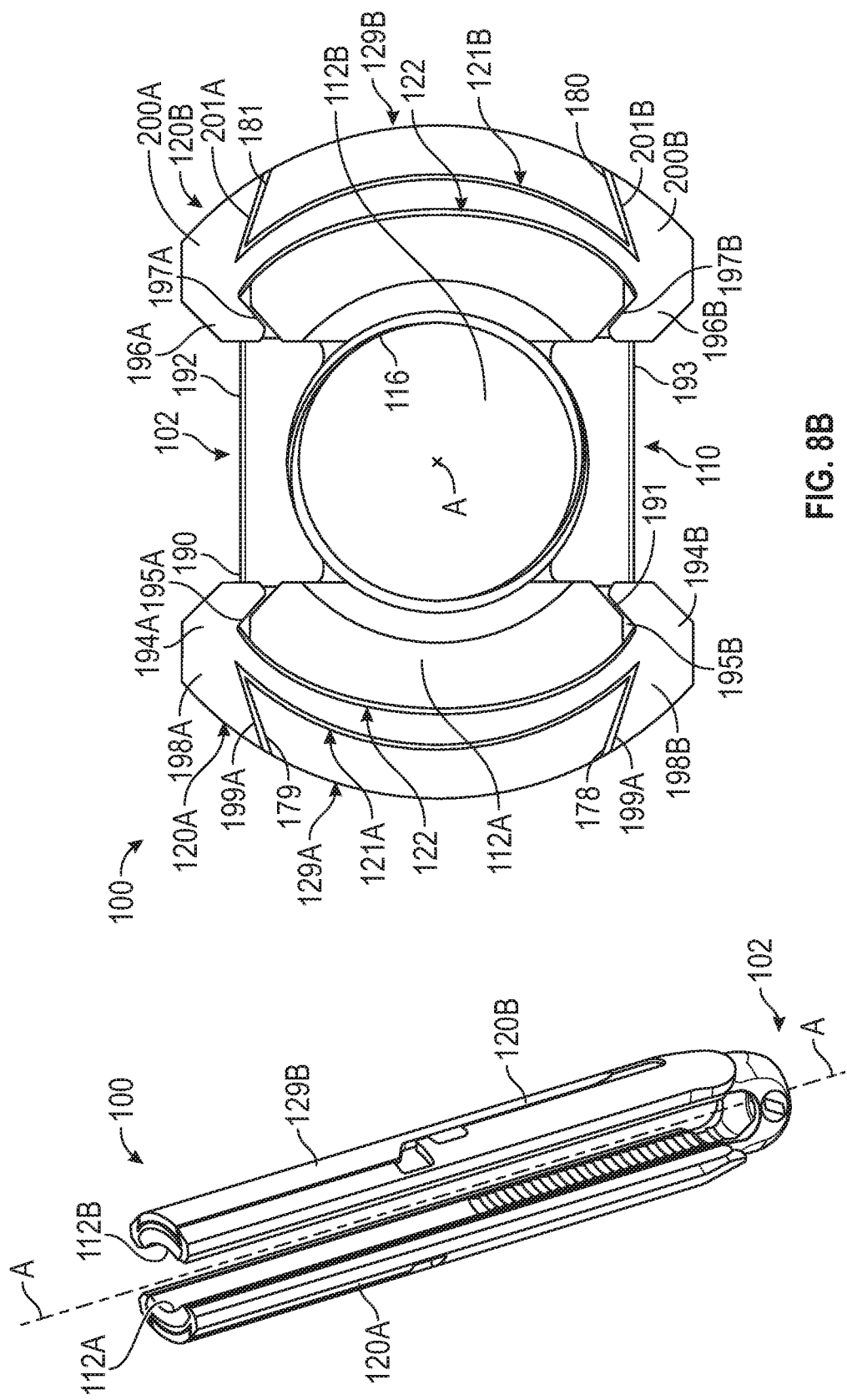

EXTENDED TAB REINFORCEMENT SLEEVE

CLAIM OF PRIORITY

This application is a continuation of U.S. patent application Ser. No. 16/693,733, filed Nov. 25, 2019, which claims the benefit of U.S. Provisional Patent Application Ser. No. 62/779,905, filed on Dec. 14, 2018, the benefit of priority of which is claimed hereby, and each of which is incorporated by reference herein in their entirety.

BACKGROUND

Orthopedic devices such as rods, plates, tethers, staples, and other devices can be used in various spinal procedures to correct abnormalities (e.g., scoliosis) or to address injuries (e.g., vertebral fracture). In some spinal procedures, anchors and rods can be secured along a spinal column between one or more vertebrae to stabilize a region of the spine. Some surgical procedures performed on the spinal column using such devices have become less invasive. However, some special parts used in minimally-invasive spinal procedures can increase the difficulty of the installation procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7A illustrates an isometric view of a slide lock of a sleeve assembly, in accordance with at least one example of this disclosure.

FIG. 7B illustrates a front view of a slide lock of a sleeve assembly, in accordance with at least one example of this disclosure.

FIG. 8A illustrates an isometric view of a cross-section of a housing portion of an anchor and a sleeve assembly, in accordance with at least one example of this disclosure.

FIG. 8B illustrates a top view of a cross-section of a portion of an anchor and sleeve assembly, in accordance with at least one example of this disclosure.

DETAILED DESCRIPTION

Figure 1A:
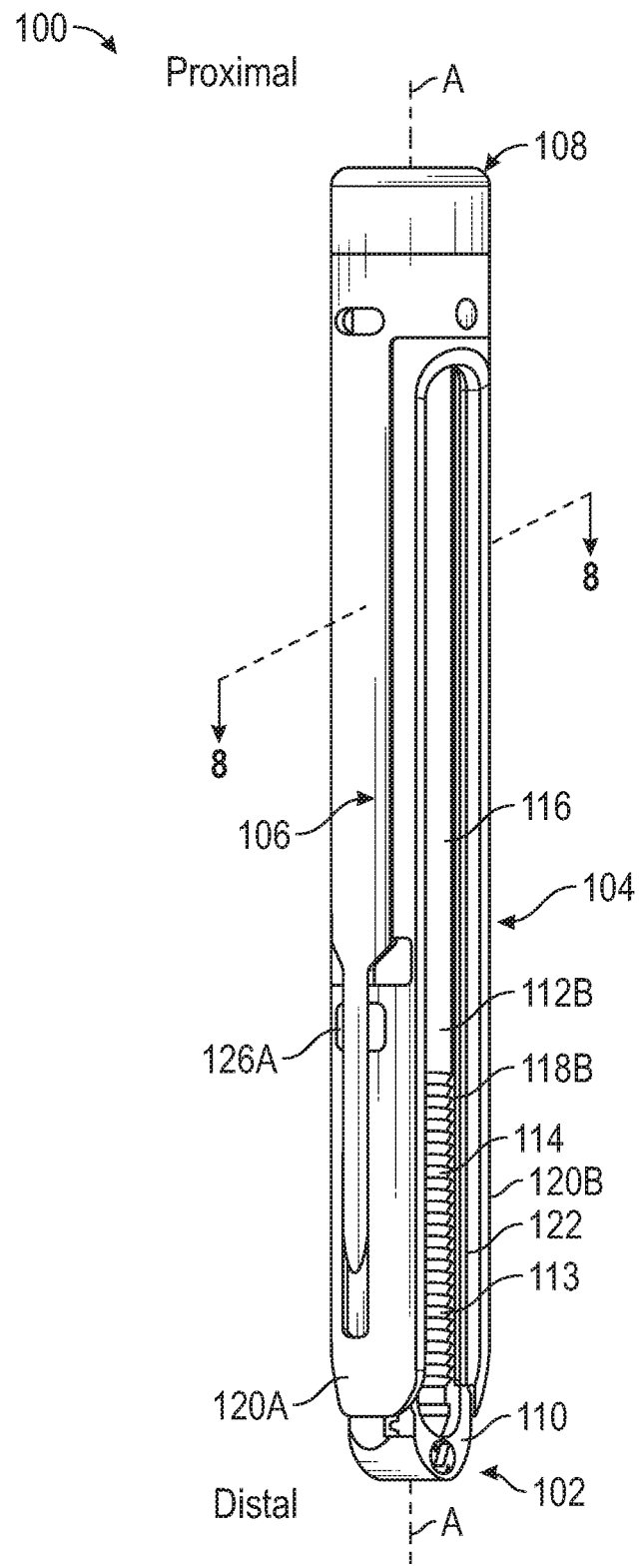
FIG. 1A illustrates an isometric view of a housing portion of an anchor and a sleeve assembly, in accordance with at least one example of this disclosure.

Bone anchors can be used together with connecting members (such as rigid and semi-rigid rods) to straighten a region of a human spine to address an abnormality (e.g., scoliosis), to stabilize a spine following an injury (e.g., fractured vertebrae), or to address degeneration of the spine caused by disease. In minimally invasive spinal procedures to address these issues, multiple small incisions can be made to form multiple small cavities near individual vertebrae. A large amount of the procedure is performed through manipulation of instruments and components extending through the small surgical cavities using special instruments that are able to be manipulated from outside of the cavities. For example, anchors are commonly driven into vertebrae, where the anchors can include extended tabs rigidly coupled to the anchors and having a length sufficient to extend outside of the cavity so that the anchors (and components engaging the anchors) can be manipulated from outside of the cavities. Because the extended tabs comprise a length sufficient to extend through the cavities, they must be separable from the heads of the anchors when the heads remain secured to vertebrae.

Some designs include two extensions each coupled to the head of the anchor at a breakaway portion, where each extended tab can be individually bent to allow separation of the extension from the head at the breakaway portions. This design requires relative movement of the extended tabs for separation. However, in some procedures, forces must be transferred from a portion of the extended tabs external to the cavity to a portion of the extended tabs in the cavity and ultimately to the head and/or shank of the anchor. However, many extended tab pedicle screws suffer from instability at the proximal end of the tabs, which can cause unwanted separation at the distal end of the tabs from the housing and can limit a surgeon's ability to manipulate the extensions.

This disclosure addresses the problem of allowing individual separation of the extended tab while allowing transfer of forces and torques through the tabs without unintended separation of the extension tabs from the head by providing a sleeve couplable to the anchor where the sleeve can transfer forces directly to and from the head of the anchor instead of to and from the extended tabs. In one example, the sleeve can include a translating lock coupled to the body of the sleeve and an actuator. An actuator can be operated to translate the lock to engage and secure the anchor to the sleeve at a point below the break-off point of the extensions. This can help to transmit forces between the sleeve and the head of the anchor (and the shank in some examples) while helping to prevent unwanted separation of the extended tabs from the head of the anchor.

This overview is intended to provide an overview of subject matter of the present patent application. It is not intended to provide an exclusive or exhaustive explanation of the invention. The detailed description is included to provide further information about the present patent application.

Figure 1B:
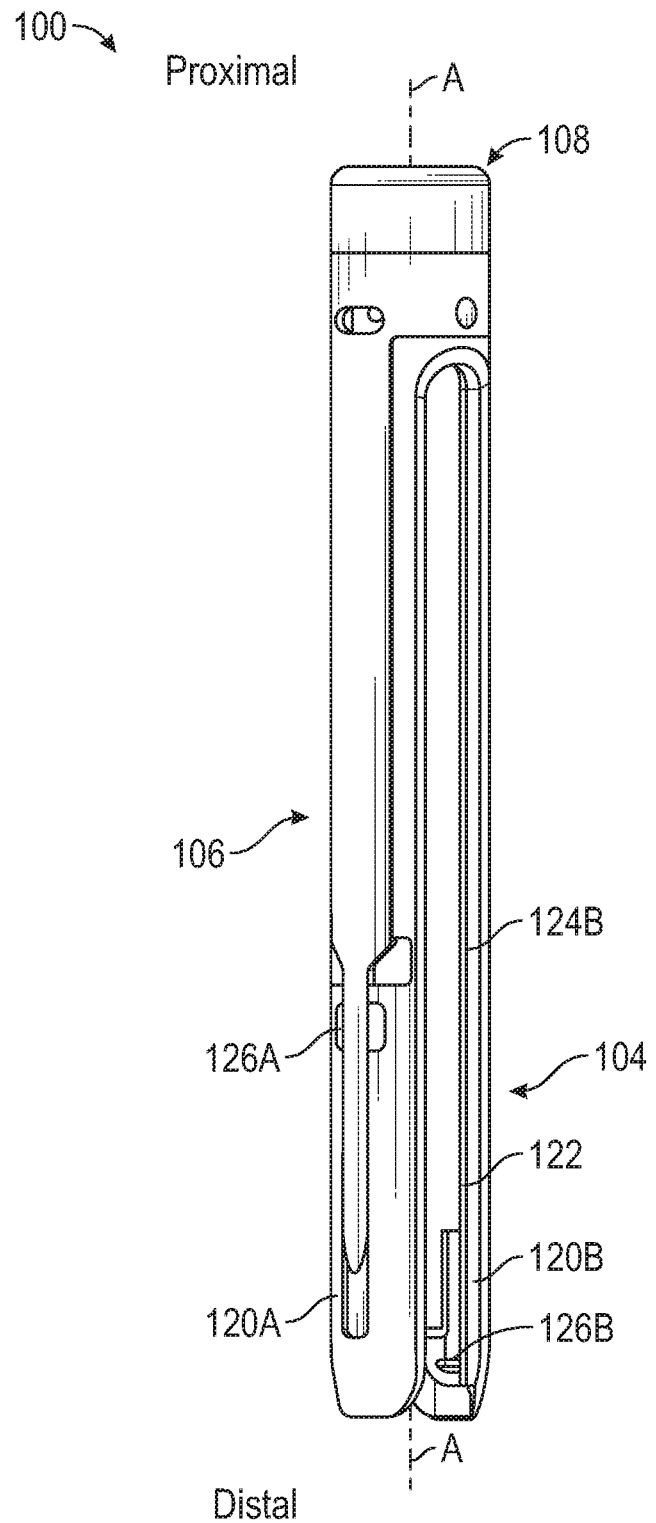
FIG. 1B illustrates an isometric view of a sleeve assembly, in accordance with at least one example of this disclosure.

FIG. 1A illustrates an isometric view of an anchor 102 and sleeve assembly 100, in accordance with at least one example of this disclosure. FIG. 1B illustrates an isometric view of a sleeve assembly 100, in accordance with at least one example of this disclosure. FIGS. 1A and 1B are discussed concurrently below.

The sleeve assembly 100 can include a body 104, a lock 106, and an actuator (or knob) 108. The anchor 102 (visible only in FIG. 1A) can include a head 110, extended tabs 112A and 112B (112A is opposite 112B, but not visible), a breakaway portion 113 (shown in FIG. 2C), a threaded portion 114, a central bore 116, and anchor slots 118A and 118B (only slot 118B is visible in FIGS. 1A and 1B). The body 104 can include a first arm 120A, a second arm 120B (referred to collectively as arms 120), a central bore 122, and sleeve slots 124A and 124B. The sleeve assembly 100 can further include spring hooks 126A and 126B. Also shown in FIGS. 1A and 1B is axis A, indicators 8-8, and orientation indicators Proximal and Distal.

The components of the anchor 102 can be comprised of rigid and semirigid materials such as metals, plastics, composites, or the like. In some examples, the anchor 102 can be comprised of bio-compatible materials, such as stainless steel, titanium, or the like. In some examples, the anchor 102 can be comprised of only one material, and can be comprised of multiple materials in other examples.

Figure 5:
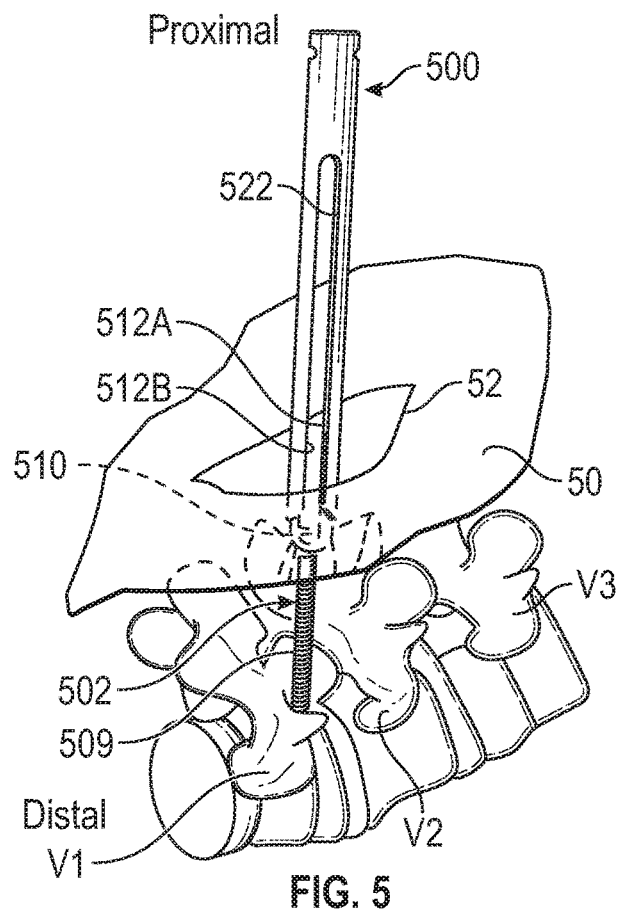
FIG. 5 illustrates an isometric view of a portion of an anchor with extended tabs, in accordance with at least one example of this disclosure.

The head 110 of the anchor 102 can be coupled to a shank, as shown in FIG. 5, at a distal portion of the head 110 with the shank extending distally therefrom and where the axis A can be a central axis for the head 110 and the shank. In other examples, the shank can deviate from the axis A at various angles. The shank can be a threaded shank or screw including male threads configured to engage bone, such as a relatively coarse thread pattern. In some examples, the shank can be configured to threadably secure to a vertebra of a spine of a human, as shown and discussed in FIG. 5 below. The shank can be an integral component to the head 110 in some examples, coupled to a distal portion of the head 110. In other examples, the shank can be a portion of a fastener that is a separate component from the head 110 and can be disposed within a bore of the head 110 and configured to be retained therein.

The anchor slots 118A and 118B of the anchor 102 can be generally U-shaped, in some examples, and can be configured to receive a connecting member (such as a connecting rod or wire) therethrough. In some examples, the head 110 can have flat sides and one or more tool interfaces, as discussed further below. The breakaway portions 113A and 113B can be a portion of the anchor 102 coupling the head 110 to the extended tabs 112A and 112B, respectively, where the breakaway portions 113 can have a thickness that is smaller than a thickness of the head 110 or the extended tabs 112A and 112B (only tab 112B is visible in FIGS. 1A and 1B) that surrounds the breakaway portions 113A and 113B. The reduced thickness of the breakaway portions 113A and 113B can facilitate separation and removal of the extended tabs 112A and 112B from the head 110.

The threaded portion 114 can be a female threaded portion within the anchor slots 118A and 118B of the head 110 and the extended tabs 112A and 112B. In some examples, the threaded portion 114 can be relatively fine threading (such as machine-type threading) configured to receive a component having male threading, such as a closure top or set screw configured to retain a connecting member or rod. The threaded portion 114 can include any known thread forms commonly utilized for pedicle screws.

The extended tabs 112A and 112B can extend substantially proximally from the head 110 and substantially parallel to axis A. Together, the extended tabs 112A and 112B can form an incomplete hollow cylinder separated by anchor slots 118A and 118B. The anchor slots 118A and 118B can be slots between the extended tabs 112A and 112B. The extended tabs 112A and 112B can be coupled to the head 110 by the break off portions 113A and 113B, as noted above.

Sleeve assembly 100 can be a generally hollow cylindrical member including the elongate body 104. The components of the sleeve assembly 100 can be comprised of rigid and semi-rigid materials such as metals, plastics, composites, or the like. In some examples, the sleeve assembly 100 can be comprised of biocompatible materials, such as stainless steel, titanium, cobalt chromium, or the like. In some examples, the sleeve assembly 100 can be comprised of only one material, and can be comprised of multiple materials in other examples.

The central bore 122 of the body 104 can be sized and shaped to receive the anchor 102 therein. The arms 120 can extend distally from the actuator 108 and can be separated by sleeve slots 124A and 124B, which can be sized to respectively align with the anchor slots 118A and 118B of the anchor 102. Each of the first arm 120A and the second arm 120B can have a length sized to extend over the extended tabs 112A and 112B of the anchor 102, while exposing part of the head 110. In some examples, first arm 120A and the second arm 120B can have a length sized to extend over the entirety of the head 110.

The lock 106 can be an elongate member secured to the body 104 and can be movable relative thereto. The lock 106 can be engaged with the actuator (or knob) 108 at a proximal portion of the lock 106, where the actuator 108 can also be secured to the body 104, but movable relative thereto. A distal portion of the lock 106 can be engageable with the spring hooks 126A and 126B, which can be biased or spring member comprised of resilient materials, such as spring steel, or the like. The spring hooks 126 can be secured to a distal portion of the body 104 and can be engaged by the lock 106 to be moved radially inward from the body 104 to engage the head 110 of the anchor 102 to secure the head 110 to the sleeve.

In operation of some examples, the extended tabs 112A and 112B can be inserted into the central bore 122 of the arms 120 with a proximal portion of the head 110 of the anchor 102 until the sleeve engages with the head 110 distally. The anchor 102 can be inserted into sleeve arms 120 either before or after the anchor 102 is inserted into a cavity and before or after the anchor 102 is secured to a bone.

Once the anchor 102 is fully inserted into the central bore 122, the knob 108 can be operated (for example, by rotating the knob) to move the lock 106 to engage and move the spring hooks such that inwardly extending projections of the spring hooks 126 are moved radially inward. The knob 108 can be rotated until the spring hooks 126 extend radially inward to fully engage a rim or channel of the head 110 to secure the anchor 110 to the body 104. By utilizing a lock with deflecting hooks, the sleeve assembly 100 provides a locking mechanism without small components (such as coil springs or pins) and with a relatively low number of parts.

In further operation of some examples, once a patient's spinal region (and specifically a vertebra) is prepared, the anchor 102 can be extended into an incision and aligned with a portion of the vertebra (for example a guide bore) configured to receive a shank. Once the shank is engaged with the guide bore in the vertebra, a torque can be applied to the head 110 about axis A using a tool to drive the shank into the vertebra. Once the shank is secured into the vertebra, a connecting member can be passed through the anchor slots 118A and 118B of the extended tabs 112A and 112B and can be reduced down through the sleeve slots 124A and 124B and into the head 110. At a later time, or during reduction, a closure top (or other fastener) can be inserted into central bore 122 of the body 104 and can be threaded into the threaded portion 114 of the anchor 102 and down to the head 110 to retain the connecting member in the head 110 of the anchor 102.

In some examples, the closure top or fastener (e.g., set screw) can be used to secure or reduce a connecting member into the head 110, with the sleeve 100 helping to prevent premature breakage at 113 during this reduction. The sleeve 100 can also be used to reinforce the extended tabs 112 to prevent unwanted break off when other external forces and torques are applied to the extended tabs 122. In one example, the sleeve 100 can reinforce the tabs 112 during hand positioning or manipulation of the anchor 100, such as when rotating an anchor already secured to a vertebral body. This type of hand positioning and rotation of the sleeve 100 and the anchor 102 can be common during a spinal de-rotation procedure, for example.

Figure 2A:
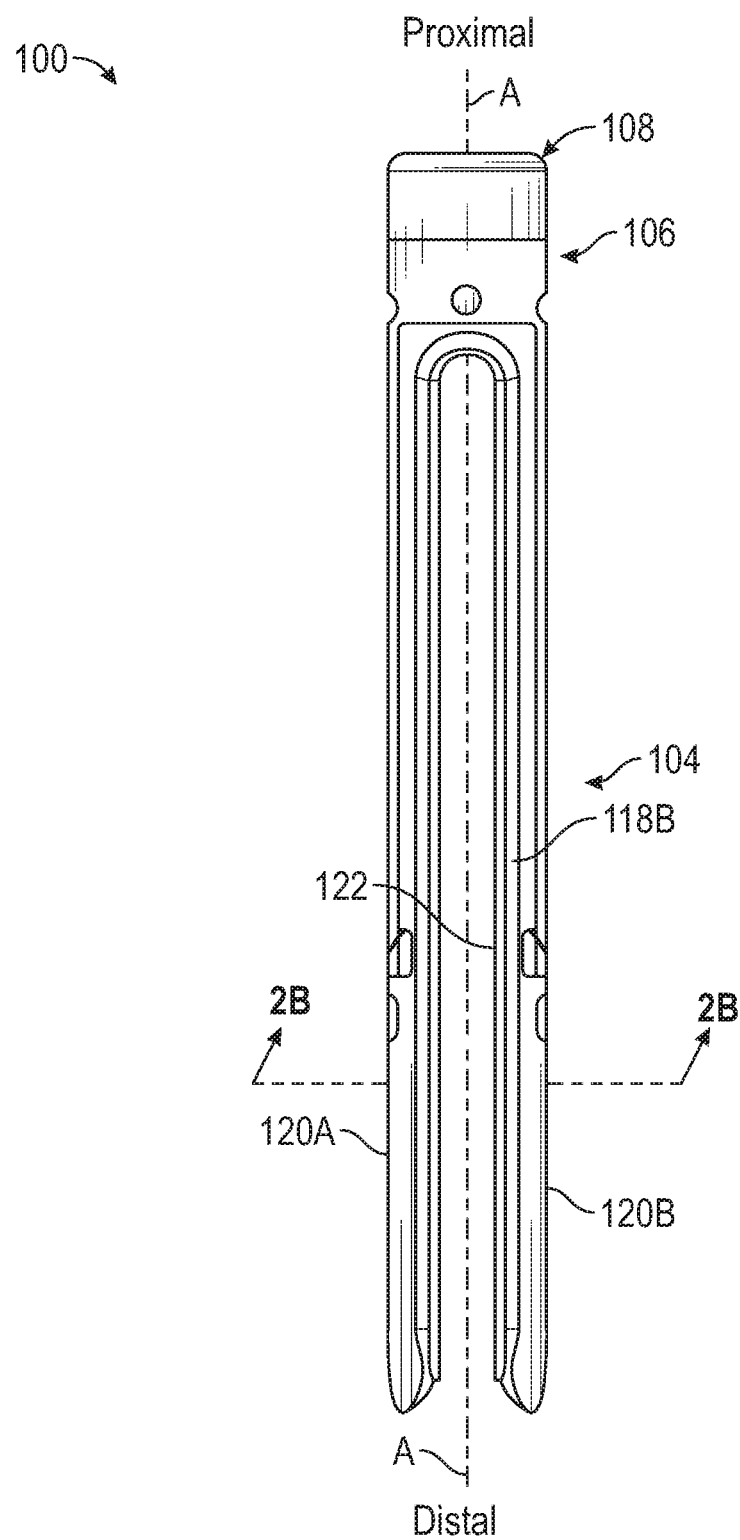
FIG. 2A illustrates a front view of a sleeve assembly, in accordance with at least one example of this disclosure.
Figure 2B:
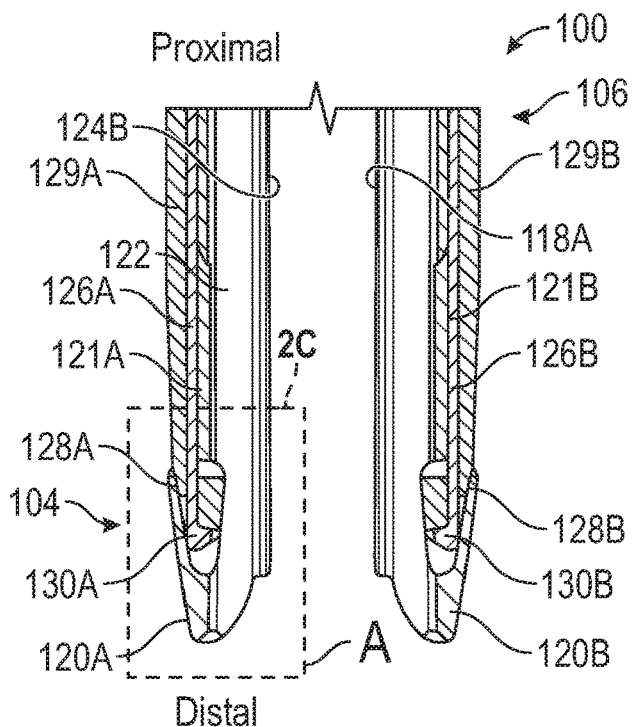
FIG. 2B illustrates a front cross-sectional view of a sleeve assembly, in accordance with at least one example of this disclosure.
Figure 2C:
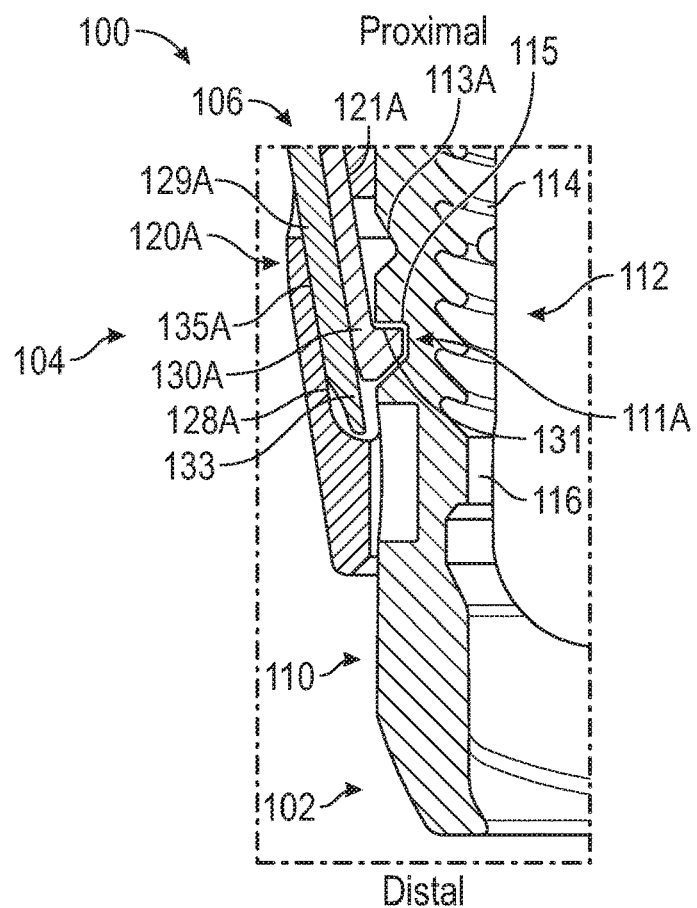
FIG. 2C illustrates a front cross-sectional view of a housing portion of an anchor and a sleeve assembly, in accordance with at least one example of this disclosure.

FIG. 2A illustrates a front view of the sleeve assembly 100, in accordance with at least one example of this disclosure. FIG. 2B illustrates a front cross-sectional view across section 2B-2B of the sleeve assembly 100, in accordance with at least one example of this disclosure. FIG. 2C illustrates a focused portion 2C front cross-sectional view of the anchor 102 and the sleeve assembly 100, in accordance with at least one example of this disclosure. FIGS. 2A-2C are discussed concurrently below.

The sleeve assembly 100 can include the body 104, the lock 106, and the actuator 108. The anchor 102 (visible only in FIG. 2C) can include the head 110, the extended tabs 112A and 112B, the breakaway portion 113, the threaded portion 114, the central bore 116, and the anchor slots 118A and 118B. The body 104 can include the first arm 120A (including a first arm channel 121A), the second arm 120B (including a second arm channel 121B), the central bore 122, the sleeve slots 124A and 124B, and pockets 128A and 128B (collectively referred to as pockets 128). The head 110 can include channels 111A and 111B (only 111A shown in FIG. 2C), which can each include a channel flat 115. The sleeve assembly 100 can further include the spring hooks 126A and 126B, which can include barbs 130A and 130B, respectively, each of which can include a barb flat 131. The lock 106 can include a first lock arm 129A and a second lock arm 129B, each of which can include a distal tapered portion 133. Also shown in FIG. 2A are axis A, section indicators 2B, and orientation indicators Proximal and Distal. Also shown in FIG. 2B are axis A, section indicator 2C, and orientation indicators Proximal and Distal. Also shown in FIG. 2C are orientation indicators Proximal and Distal The sleeve assembly 100 and the anchor 102 can be similar to the sleeve assembly 100 and the anchor assembly 102 of FIGS. 1A and 1B; however, FIGS. 2A-2C show additional details of the sleeve assembly 100 and the anchor 102. For example, FIG. 2B shows pockets 128A and 128B of arms 120A and 120B, respectively, where each of the pockets 128 is located at a distal portion of each of the arms 120 and each pocket 128 is connected to one of the arm channels 121. For example, the first pocket 128A is connected to a distal portion of the first arm channel 121A and the second pocket is connected to a distal portion of the second arm channel 121B.

Each pocket 128 can be a cavity open to the central bore 122 of the body 104 and can extend radially outward therefrom. Each pocket 128 can be sized to receive one lock arm 129 and one spring hook 126 therein. In some examples, each pocket 128 can be sized such that when the lock arm 129 and spring hook 126 are disposed within the pocket and when the barb 130 is engaged with the channel 111, there is relatively little space between a radially outer wall of the pocket, the lock arm 129, the spring hook 126, and the head 110 of the anchor. The tolerance stackup between the pocket 128 and the lock arm 129, spring hook 126, and barb 130 can range from a clearance fit to an interference fit, depending upon how tightly the sleeve assembly 100 needs to be connected to the anchor 110. This can help to limit radially outward movement of the spring hook 126 when the lock arm 129 is in a locked position, helping to prevent the spring hook 126, and therefore the sleeve assembly 100, from disengaging the head 110. The low gap between these components can also help to transfer forces and stress between the head 110 and the sleeve assembly 100, which can further help limit bending of the anchor 102 and the sleeve assembly. Further, the arm 129 can act as a wedge within the pocket 128 to drive the spring hook into position by engaging the pocket 128 and a radially outer portion of the spring hook 126.

FIG. 2C also shows the channel 111A of the head 110, which can be sized and shaped to receive the barb 130A when the lock arm 129A is in a locked position. When in the locked position, the barb flat 131 can engage the channel flat 115 to help limit proximal translation of the sleeve assembly 100 relative to the head 110. The barb flat 131 can extend substantially around a perimeter of the head 110, in some examples, and can be flat or planar from a proximal perspective. Similarly, the barb flat 131 can be flat or planar from a proximal perspective. In other examples, the barbs 130 can be of other shapes, such as a hook, to further help limit relative movement of the sleeve assembly 100 relative to the head 110 of the anchor 102. A distal surface 165 connecting the barb to the distal tip 164 can be rounded to help improve disengagement of the barb 131 from the head 110. In other examples, the distal surface 165 can be flat.

FIGS. 2B and 2C also show the distal tapered portion 133 of each lock arm 129. As shown in FIG. 2B, the distal tapered portion 133 can rest at a proximal portion of the pocket 128 when the lock 106 is in an unlocked position (for example, when the lock arm 129A is translated proximally).

In operation of some examples, the lock 106 can be in the unlocked position, as shown in FIG. 2B, where the lock 106 is translated proximally sufficiently to allow the spring hooks 126 to be locked within the pockets 128. That is, each spring hook 126 does not extend into the central bore 122 when the lock 106 is in the unlocked position. When it is desired to secure the sleeve assembly 100 to the anchor 102, the head 110 of the anchor 102 can be inserted into the central bore 122 of the sleeve assembly, as described above with respect to FIGS. 1A and 1B. When the anchor 102 is completely inserted into the central bore 122, the channels 131 of the anchor can align with the pockets 128. At this point, the actuator 108 (or knob) can be rotated to cause distal translation of the lock 106. Distal translation of the lock 106 causes distal translation of the lock arms 129 within their respective lock slots 121A.

Because the distal portion 133 of each lock arm 129 is tapered and rests at a proximal opening of each pocket in the unlocked position of the lock 106, the lock arms 129 thereby retain their position within the pocket 128 while allowing the spring hooks 126 to be disengaged from the head 110 and to be located within the pocket 128 when the lock arms 129 are in the unlocked (proximal) positions.

As the lock arms 129 extend into the pockets 128 (as shown in FIG. 2C), an outer wall 135 of the pockets 128 guide the lock arms 129 to deflect radially inward to contact the spring hooks 126, which causes the spring hooks 126 to move radially inward. Because each outer wall 135 is angled, the spring hooks 126 are deflected further radially inward as the lock arms 129 are translated further distally into the pockets 128, causing the barbs 130 of the spring hooks to extend radially inward from the pockets 128 into the central bore 122 to engage the channels 111 of the head 110 of the anchor. The radially inward extension of the spring hooks 126 can be limited by contact between the barb 130 and the channel 111 and/or the spring hooks 126 and the head 110, and/or by contact between a distal portion of the pockets 128 and a distal end of the tapered portion 133 of the lock arms 129.

When the lock 106 is in the locked position, proximal translation of the head 110 relative to the sleeve assembly 100 is limited by contact between the extended tabs 112 and the body 104, distal translation of the head 110 relative to the sleeve assembly 100 is limited by engagement of the barbs 130 with the channel 111, and movement transverse to the axis A of the head 110 relative to the sleeve assembly 100 is limited by contact between the anchor 102 and the body 104, thus securing the anchor 102 to the sleeve assembly 100 when the lock 106 is in the locked position. Because the channels 111 are positioned distally of the breakaway portions 113 of the extended tabs 112, interaction between the sleeve assembly 100 and the head 110 (that is, interaction between the spring hooks 126 and the head 110) is less likely to cause unwanted separation of the extended tabs 112 from the head 110 during manipulation of the sleeve assembly 100 during a procedure.

When it is desired to disengage the sleeve assembly 100 from the anchor 102, the actuator 108 can be operated to translate the lock 106 proximally, causing the lock arms 129 to move proximally, such that the arms 129 will move out of the pockets 128 enough to allow the spring hooks 126 to retract into the pockets 128 while disengaging from the channel 111 of the head 110. In some examples, the spring hooks 126 can be biased to a retracted position, as shown in FIG. 2B, so that when the force applied by the lock arms 129 is removed, the spring hooks 126 retract into the pockets 128 without the application of a force external to the spring hooks 126.

When the barbs disengage from the channel 111 of the head 110, the anchor 102 can be translated distally relative to the sleeve assembly 100, allowing the anchor 102 to be removed, if desired. Because the pockets 128 (together with the anchor 102) substantially surround the spring hooks 126, the pockets 128 help to protect the spring hooks 126 from interference from tissue of a patient, where such interference can prevent the sleeve assembly 100 disengaging from the anchor 102. The pockets 128 therefore help to ensure the sleeve assembly 100 can be removed from the anchor 102, as desired.

Figure 3A:
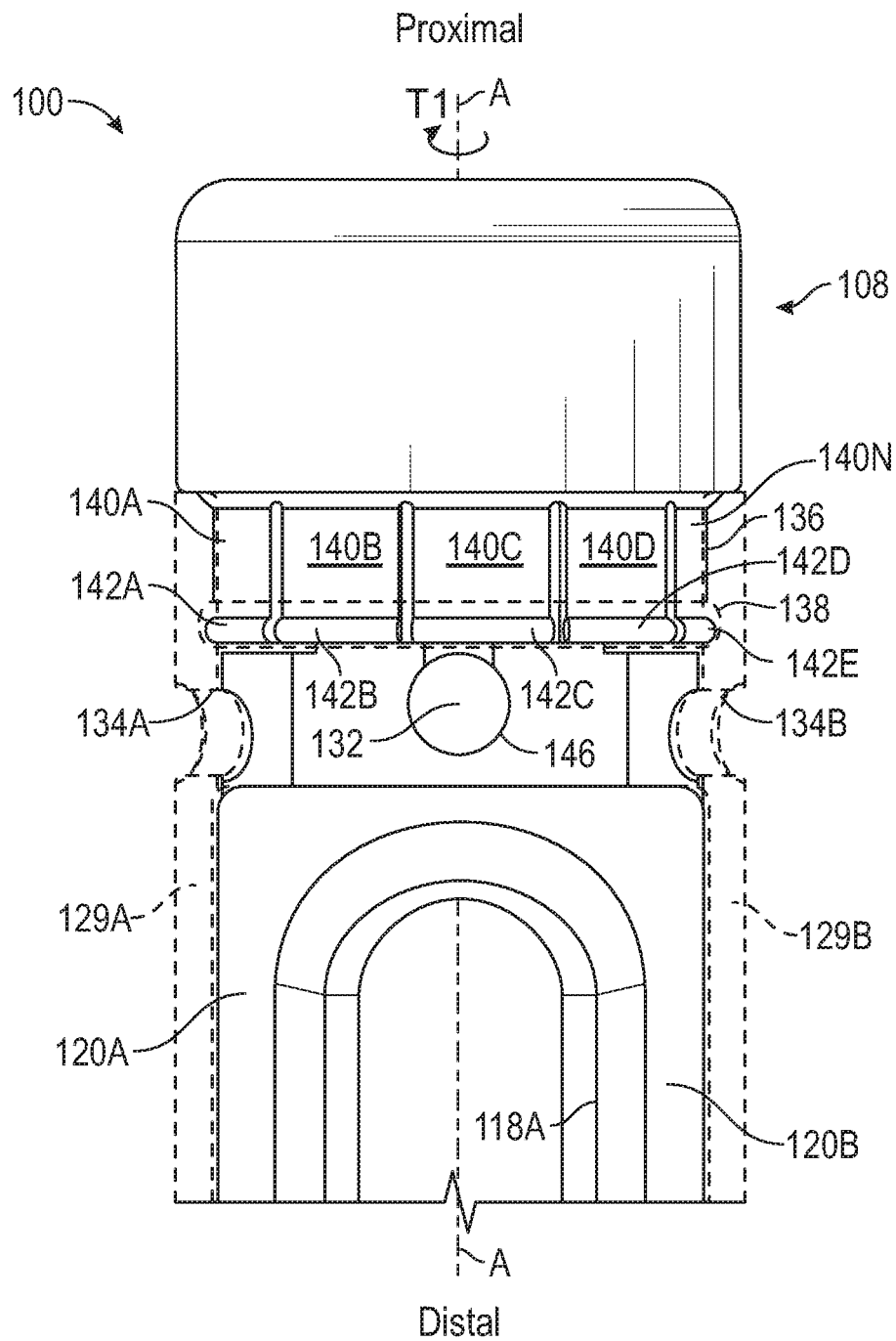
FIG. 3A illustrates a front view of a sleeve assembly with a portion of the sleeve assembly in phantom, in accordance with at least one example of this disclosure.
Figure 3B:
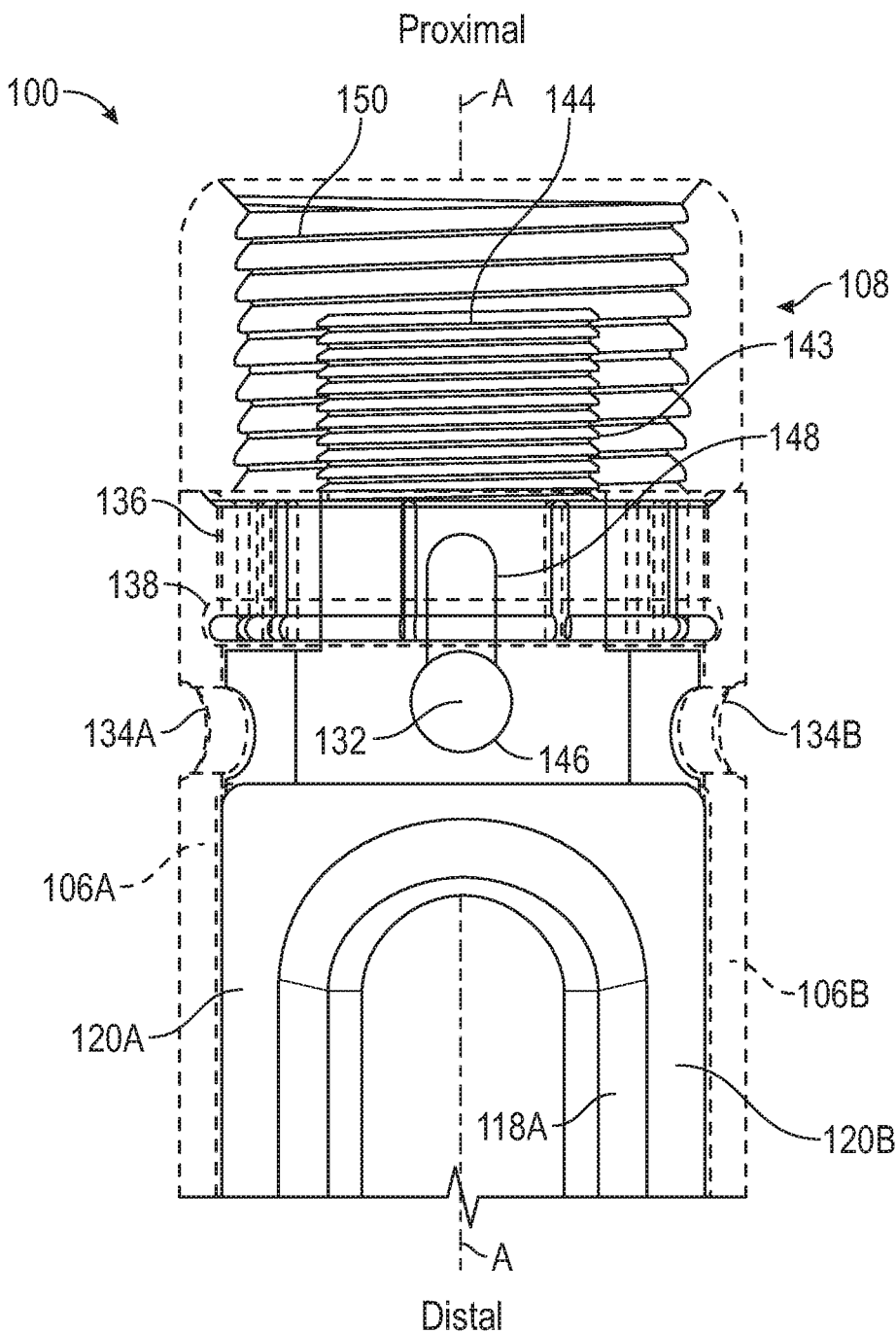
FIG. 3B illustrates a front view of a sleeve assembly with a portion of the sleeve assembly in phantom, in accordance with at least one example of this disclosure.

FIG. 3A illustrates a front view of the sleeve assembly 100 with a portion of the sleeve assembly in phantom, in accordance with at least one example of this disclosure. FIG. 3B illustrates a front view of the sleeve assembly 100 with a portion of the sleeve assembly in phantom, in accordance with at least one example of this disclosure. FIGS. 3A and 3B are discussed below concurrently.

The sleeve assembly 100 of FIGS. 3A and 3B can be consistent with the sleeve assembly of FIGS. 1A-2C, but FIGS. 3A and 3B can show additional details of the sleeve assembly. For example, FIGS. 3A and 3B show how the actuator 108, body 104, and lock 106 are connected and how they interact.

FIGS. 3A and 3B show pin 132, which can be a rigid or semi-rigid elongate fastener, such as a cylindrical pin, rivet, screw, or the like. The pin 132 can pass through a pin bore 146 of the lock 106 and can also pass through a pin channel 148 of the body 104 to couple the lock 106 to the body 104. The pin channel 148 can have an axial length longer than a diameter of the pin 132 to allow the pin to move in a direction substantially parallel to axis A. This movement can permit the lock 106 to move axially relative to the body 104. The pin channel 148 can also be sized to have a width similar to the diameter of the pin 132 to help limit non-axial movement of the lock 106 with respect to the body 104.

FIGS. 3A and 3B also show that lock 106 can include a proximal bore 136 and an undercut 138, which can be sized and shaped to receive tabs 140A-140N (collectively referred to as tabs 140) and projections 142A-142N (collectively referred to as projections 142), respectively. The undercut 138 can be spaced away from a proximal end of the lock 106 such that once the projections 142 are disposed within the undercut 138, axial movement of the actuator 108 is limited proximally and distally with respect to the lock 106.

FIGS. 3A and 3B also show that actuator 108 includes internal threading 150, which can be complementary to external threading 144 of a proximal portion 143 of the body 104. Interaction (screwing and unscrewing, for example) of internal threading 150 of the actuator can engage the external threading 144 of the proximal portion of the body 143 to cause movement of the actuator 108 relative to the body 104.

For example, during operation of the sleeve assembly 100, a torque T1 about axis A can be applied to the actuator 108 to screw the internal threading 150 of the actuator 108 onto the internal threading 144 of the proximal portion 143 of the body 104. Because the actuator 108 is coupled to the lock 106 via tabs 140, as the actuator 108 screws further (distally) onto the body 104, the lock 106 (and the lock arms 129) are translated distally with respect to the body, allowing the lock arms 129 to engage the spring hooks 126, as discussed above. When it is desired to unlock the spring hooks 126 from the anchor 102, the actuator 108 can be rotated in a direction opposite the torque T1 to translate the actuator 108 and the lock 106 proximally with respect to the body 104. By providing a threaded interface to operate the actuator 108 to control translation of the lock 106, the relatively small translation of the lock 106 with respect to the body is given a relatively high degree of controllability to the user while also providing user feedback during tightening and loosening.

FIGS. 3A and 3B also show tool interfaces 134A and 134B, which can be bores in the lock 106 and/or the body 104, where the tool interfaces can support another tool, such as a reducer, counter-torque, or de-rotator, for example.

Figure 4A:
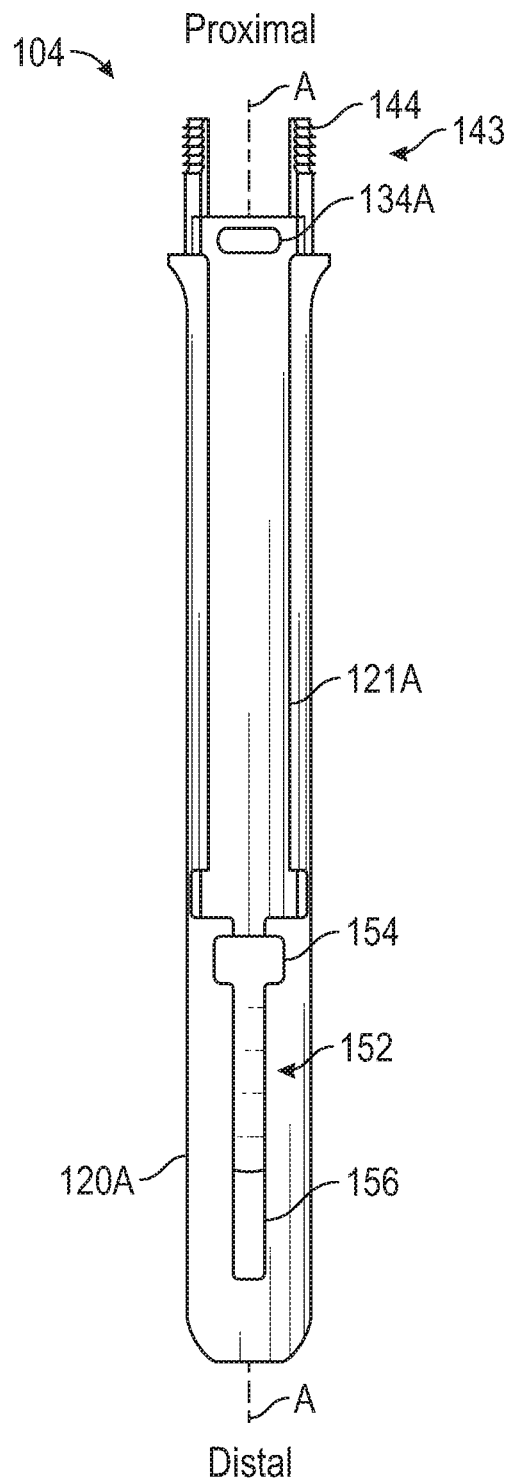
FIG. 4A illustrates a side view of a portion of a sleeve assembly, in accordance with at least one example of this disclosure.
Figure 4B:
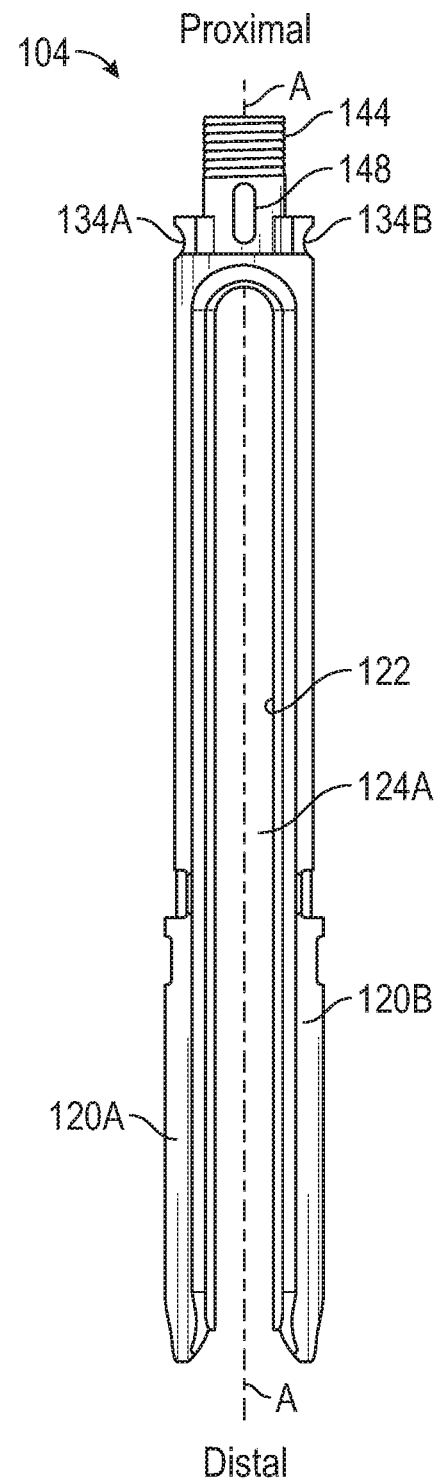
FIG. 4B illustrates a front view of a portion of a sleeve assembly, in accordance with at least one example of this disclosure.
Figure 4C:
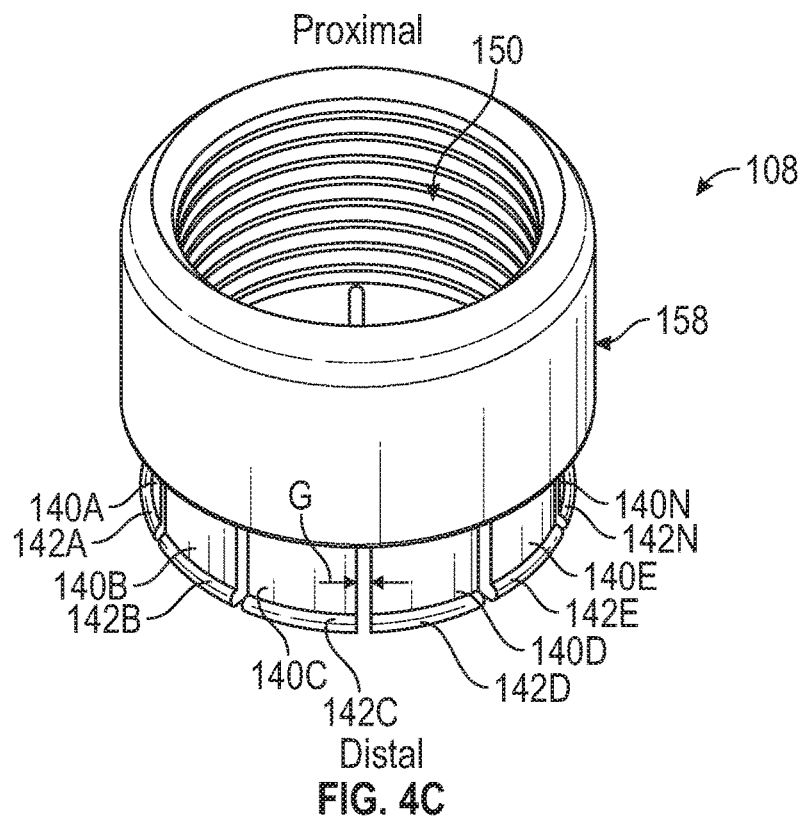
FIG. 4C illustrates an isometric view of a cap of a sleeve assembly, in accordance with at least one example of this disclosure.

FIG. 4A illustrates a side view of a portion of the body 104 of the sleeve assembly 100, in accordance with at least one example of this disclosure. FIG. 4B illustrates a front view of a portion of the body 104 of the sleeve assembly 100, in accordance with at least one example of this disclosure. FIG. 4C illustrates an isometric view of the knob 108 of the sleeve assembly 102, in accordance with at least one example of this disclosure. FIGS. 4A-4C are discussed below concurrently.

The sleeve assembly 100 of FIGS. 4A-4C can be consistent with the sleeve assembly of FIGS. 1A-3B, but FIGS. 4A-4C show additional details of the sleeve assembly. For example, FIGS. 4A and 4B show the proximal portion 143 of the body 104 extending proximally from the body arms 120A and 120B, where the male threaded portion 144 extends to a proximal end of the body 104. The proximal portion 143 can include a pair of proximal arms extending from the body 104, offset from the body arms 120. In other examples, the proximal arms of the proximal portion 143 can be aligned with the body arms 120.

FIG. 4B also shows the pin channel 148 extending proximally to distally along axis A where the pin channel 148 can terminate proximally before the threaded portion 144. FIG. 4A further shows tool interface 134A which can be a slot or bore extending substantially perpendicular to the axis A.

Also shown in FIG. 4A is a spring hook channel 152, which can include a proximal portion 154 and a distal portion 156. The proximal portion 154 can have a width substantially wider than a width of the distal portion 156 for receiving a head or wings of the spring hook 126, as discussed further below. Though the spring hook channel 152 is shown as being a substantially T-shaped channel, the spring hook channel 152 can be of other shapes, such as an I-shape, a J-shape, or the like. In some examples, the spring hooks 126 can be secured to the body 104, such as by laser-welding, within the spring hook channels 152, such as at the proximal portion 154 to provide a flex of the spring hook 126 relative to the body 104.

FIG. 4C shows additional details of the actuator 108 such as a knob portion 158 and the fingers 140 (each including the tabs 142). The knob portion 148 can be substantially cylindrical in some examples, and can have other shapes in other examples, such as hexagonal, octagonal, or the like. The fingers 140 can each extend distally from the knob portion 158 and can be in a cantilevered arrangement therewith.

Each of the fingers 140 can be circumferentially spaced. For example, finger 140C can be spaced from finger 140D by a gap G, which can allow the fingers 140 to deflect radially inward for attachment of the actuator 108 to the locking portion 106. The number of fingers can be any number, such as 2, 3, 4, 5, 6, 7, 8, 9, 10, 12, 15, 20, or the like. Similarly, the gap G can be varied for a desired number of fingers and for a desired radially inward deflection of the fingers 140. The projections 142 of the fingers 140 can extend radially outward therefrom at a distal portion (and in some examples at a distal termination) of each of the fingers 140.

FIG. 5 illustrates an isometric view of an anchor 502 with a sleeve assembly 500, in accordance with at least one example of this disclosure. The anchor 502 can include a shank 509, a head 510, and extensions 512A and 512B. Also shown in FIG. 5 are a cutaneous portion 50, an opening 52, and vertebrae V1, V2, and V3.

The anchor 502 of FIG. 5 can be consistent with the anchors discussed above. Similarly, the sleeve assembly 500 can be consistent with the sleeve assembly 100 discussed above with respect to FIGS. 1-4C. FIG. 5 shows how the sleeve assembly 500 and the anchor 502 can be used in an example operation. In operation of some examples, an incision can be made on a posterior portion of a patient along the patient's vertebral column, for example, along the patient's thoracic spine. For example, an incision can be made on the cutaneous portion 50 where the incision extends through the dermis and subcutaneous tissue to create the opening 52 and exposes or partially exposes the vertebrae V1-V3. In some cases, multiple incisions can be made to minimize invasion. Next, a punch may be used to break the cortical bone to create a pilot or guide hole in a vertebra for the anchor 502. Once the vertebra (for example, the vertebra V1) is prepared, the anchor 502 can be extended into the opening 52 such that the anchor 502 can be engaged with the vertebra V1, for example. The shank 509 of the anchor 502 can then be driven into, for example, a pedicle of the vertebra V1 to secure the anchor 502 to the vertebra V1 while the anchor and the sleeve 502 can extend beyond the opening 52.

While in this position, the extended tabs 512 can receive the sleeve assembly 500 thereon. In other examples, the sleeve assembly 500 can be secured to the anchor 502 prior to securing the anchor 502 to the vertebra V2. Once the sleeve assembly 500 is secured to the anchor 502, the sleeve assembly 500 can be manipulated by hand (or tool) to position vertebra V1, such as during a de-rotation procedure. During this rotation, the sleeve assembly 500 can help prevent unwanted separation of the extended tabs 512 from the head 510 of the anchor 502, where the lock of the sleeve assembly 500 can help to prevent such separation.

Figure 6C:
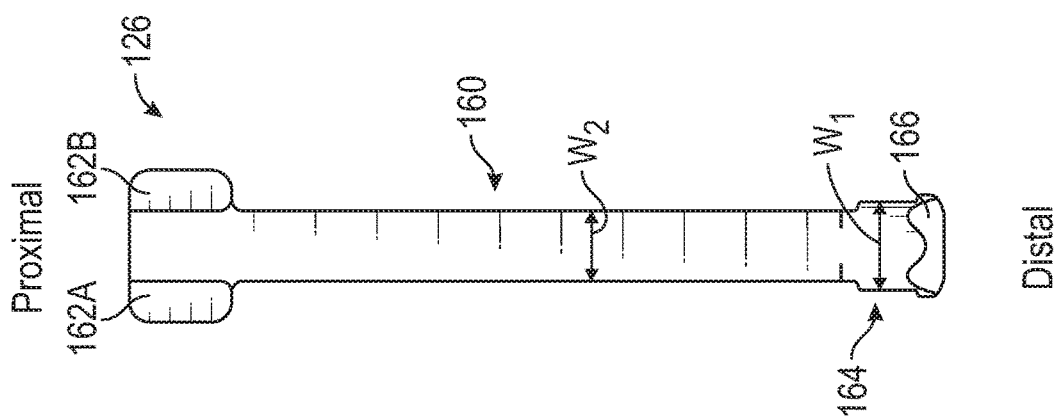
FIG. 6C illustrates a front view of a spring hook of a sleeve assembly, in accordance with at least one example of this disclosure.
Figure 6B:
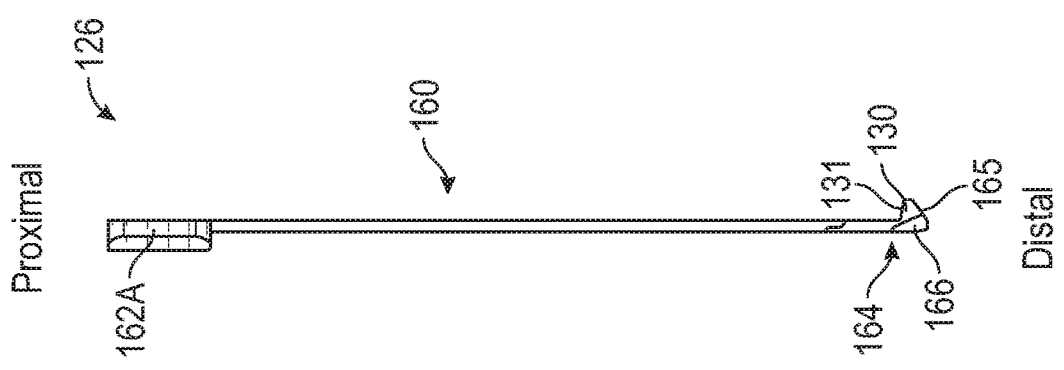
FIG. 6B illustrates a side view of a spring hook of a sleeve assembly, in accordance with at least one example of this disclosure.
Figure 6A:
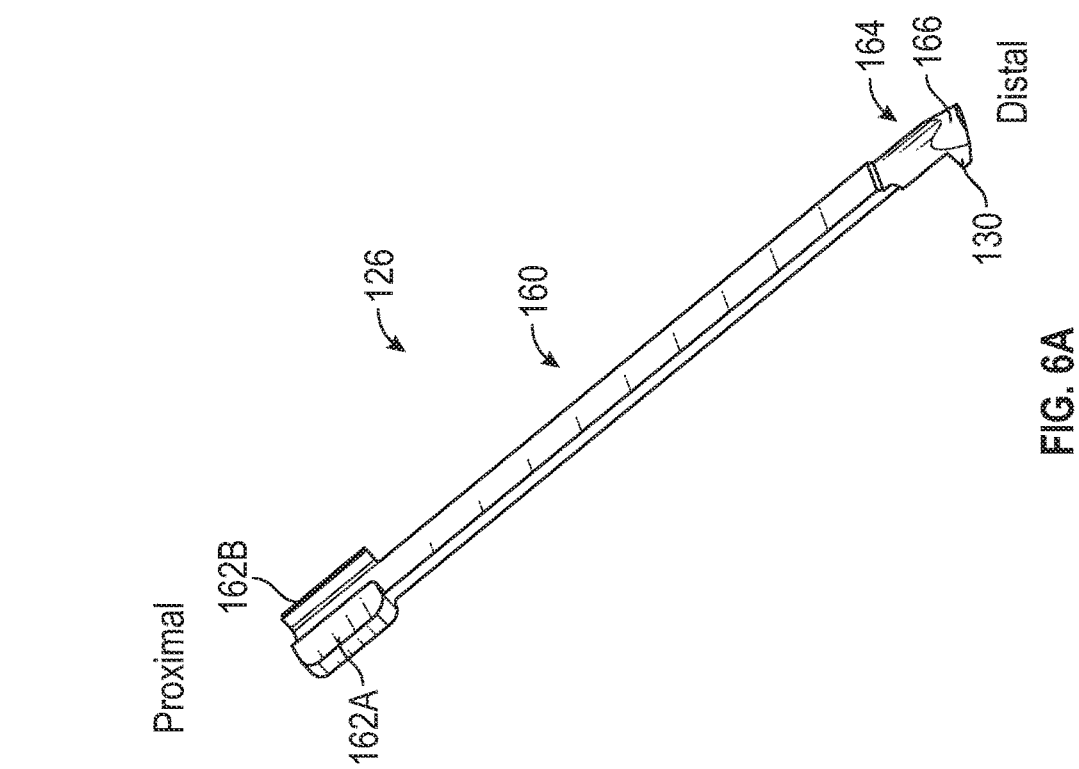
FIG. 6A illustrates an isometric view of a spring hook of a sleeve assembly, in accordance with at least one example of this disclosure.

FIG. 6A illustrates an isometric view of the spring hook 126, in accordance with at least one example of this disclosure. FIG. 6B illustrates a side view of the spring hook 126, in accordance with at least one example of this disclosure. FIG. 6C illustrates a front view of the spring hook 126, in accordance with at least one example of this disclosure. FIGS. 6A-6C are discussed below concurrently.

The spring hook 126 can include the barb 130 (including the flat 131), a body 160, tabs 162A and 162B (collectively referred to as tabs 162), and a distal tip 164, which can include the barb 130, and a tapered portion 166.

The spring hook 126 of FIGS. 6A-6C can be consistent with the spring hook 126 of FIGS. 1-4C, except that FIGS. 6A-6C show additional details of the spring hook 126. As discussed above, the spring hook 126 can be comprised of resilient materials, such as steels, titanium alloys, or the like. Each of the components of the spring hook can be comprised of a single material in some examples, and can be an assembly comprised of multiple materials in other examples.

The body 160 can be substantially thin and elongate and can be connected to tabs 162 at a proximal portion of the body 160 and the distal tip 164 at a distal portion of the body 160. The tabs 162 can respectively extend outward from the body (in substantially opposing directions). The tapered portion 166 of the distal tip 164 can be tapered toward the barb 130 as the distal tip 164 extends distally. In some examples, the tapered portion 166 of the distal tip 164 can have a taper that is sized and shaped to substantially match an angle of the outer wall 135 of the pockets 128 of the sleeve body 120 to help reduce engagement and friction between the spring hook and the outer wall 135. Also, a width W of the distal tip 164 can be wider than the distal portion 156 of the opening of the hook channel 152 to limit radially outward movement of the distal tip 164.

Figure 7D:
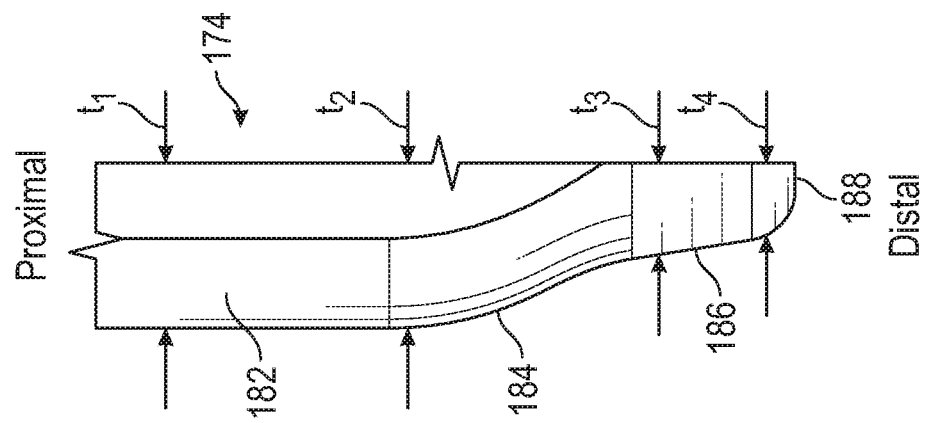
FIG. 7D illustrates a front view of a portion of a slide lock of a sleeve assembly, in accordance with at least one example of this disclosure.
Figure 7C:
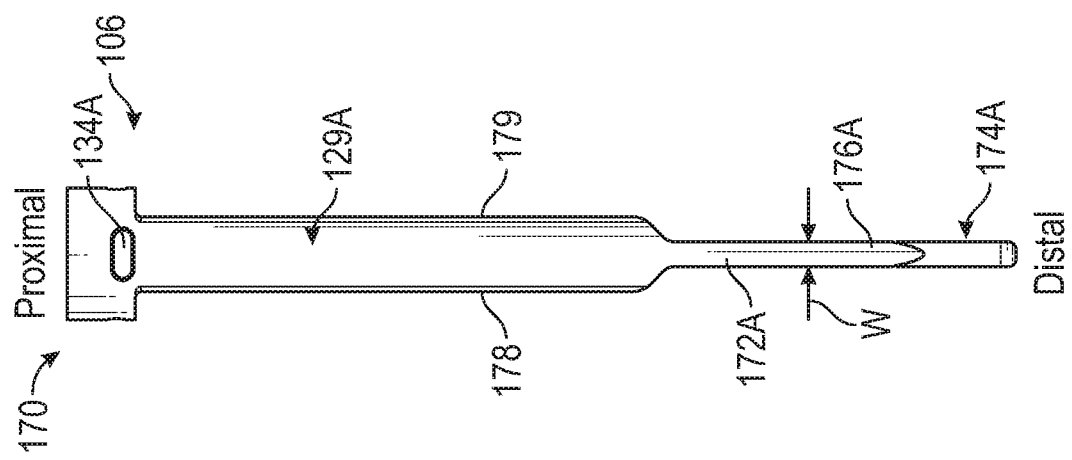
FIG. 7C illustrates a side view of a slide lock of a sleeve assembly, in accordance with at least one example of this disclosure.

FIG. 7A illustrates an isometric view of the lock 106 of the sleeve assembly 102, in accordance with at least one example of this disclosure. FIG. 7B illustrates a front view of the lock 106 of the sleeve assembly 102, in accordance with at least one example of this disclosure. FIG. 7C illustrates a side view of the lock 106 of the sleeve assembly 102, in accordance with at least one example of this disclosure. FIG. 7D illustrates a front view of a portion of the lock 106 of the sleeve assembly 102, in accordance with at least one example of this disclosure. FIGS. 7A-7D are discussed below concurrently.

The lock 106 can include a proximal portion 170 and the lock arms 129A and 129B. The proximal portion 170 can include the tool interfaces 134A and 134B, and the pin bore 146. The lock arms 129A and 129B can include distal portions 172A and 172B, respectively. The distal portions 172A can each include a distal tip 174, partially formed by cut portion 176. Also, the lock arm 129A can include chamfers 178 and 179 and the lock arm 129B can include chamfers 180 and 181. The distal tip 174 can include a first portion 182, a second portion 184, a third portion 186, and a fourth portion 188. Also shown in FIGS. 7A-7D are width W, thicknesses t1, t2, t3, and t4, and orientation indicators Proximal and Distal.

The distal portions 172 of the lock arms 129 can be of a width W relatively smaller than that of a width of the proximal portion of the lock arms 129 to help allow the distal portions 172 to deflect radially inward for insertion into the pocket 128 of the body 104 during locking and unlocking operations. The distal tip 174 can also be sized and shaped for insertion into the pockets, as discussed further below. Also, the chamfers 178-181 can be sized and shaped to be retained by the body (for example, in a dovetail arrangement), as discussed below with respect to FIGS. 8A-8B.

The distal tip 174 can include four portions of varying thicknesses, in some examples. The first portion 182 can have the first thickness t1; the second portion 184 can have the second thickness t2; the third portion 186 can have the third thickness t3, and, the fourth portion 188 can have the fourth thickness t4. In some examples, the thicknesses t1, t2, t3, and t4 can all be different where the fourth thickness t4 is smaller than the third thickness t3, which is smaller than the second thickness t2, which is smaller than the first thickness t1. In other examples, some or all of the thicknesses t1-t4 can be the same thickness. In some examples, each of the first portion 182, the second portion 184, the third portion 186, and the fourth portion 188 can be tapered from a larger to smaller thickness as the distal tip portion 174 extends proximally to distally. Such a tapered profile of the distal tip portion 174 can allow for the spring hook 126 to bias radially outward in an unlocked position within the pocket 128 of the body 104. That is, the third portion 186 can also have the thickness t3 to allow the third portion 186 to rest within a proximal portion (or proximal entrance) of the pocket 128 when the lock 106 is in an unlocked position to retain the lock 106 while allowing the spring hook 126 to extend radially outward to allow for clearance for the head 110 of the anchor 102 to enter the central bore 122.

Though four portions of the distal tip 174 are shown, the distal tip 174 can have fewer portions (such as 1, 2, or 3 portions) or more portions. Also, the thicknesses and tapers of the portions of the distal tip 174 can vary in other examples.

FIG. 8A illustrates an isometric cross-sectional view of the anchor 102 and the sleeve assembly 100 across indicators 8-8 of FIG. 1A, in accordance with at least one example of this disclosure. FIG. 8B illustrates a top view of a cross-section of the anchor 102 and the sleeve assembly 100 across indicators 8-8 of FIG. 1A, in accordance with at least one example of this disclosure.

The anchor 102 and the sleeve assembly 100 can be consistent with the anchor and sleeve assemblies discussed above; however, FIGS. 8A and 8B show additional details of the anchor 102 and the sleeve assembly 100. For example, FIG. 8B shows show the extended tabs 112A and 112B of the anchor 102 can be secured to the body 104 using chamfered (or dovetailed) portions.

Each of the extended tabs 112A and 112B can include chamfered portions. The extended tab 112A can include chamfers 190 and 191 and the extended tab 112B can include chamfers 192 and 193. The body 104 can include radially inward extending projections, where each projection has a chamfer complimentary to the chamfers of the extended tabs 112A and 112B. The arm 120A can include inner projections 194A and 194B, which can respectively include faces 195A and 195B. The arm 120B can include inner projections 196A and 196B, which can respectively include faces 197A and 197B.

The face 195A can engage the chamfer 190 and the face 195B can engage the chamfer 191 in a dovetail-type arrangement to retain the extended tab 112A in the central bore 122, by preventing movement of the extended tab 112A in directions non-parallel to axis A, while still allowing translation of the extended tab 112A with respect to the body 104 parallel to the axis A. Similarly, the face 197A can engage the chamfer 192 and the face 197B can engage the chamfer 193 in a dovetail-type arrangement to retain the extended tab 112B in the central bore 122, by preventing movement of the extended tab 112B in directions non-parallel to axis A, while still allowing translations of the extended tab 112B with respect to body 104 parallel to the axis A. Generally, this arrangement can allow for insertion of the anchor 102 into the body 104 and can prevent non-axial movement of the anchor 102 with respect to the body.

FIGS. 8A and 8B also show how the lock 106 can be secured to the body 104. The lock arm 129A can include chamfers 178 and 179 and the lock arm 129B can include chamfers 178 and 179. The body 104 can include radially outward extending projections, where each projection has a chamfer complimentary to the chamfers of the lock arms 129A and 129B. The arm 120A can include outer projections 198A and 198B, which can respectively include faces 199A and 199B. The arm 120B can include outer projections 200A and 200B, which can respectively include faces 201A and 201B.

The face 199A can engage the chamfer 179 and the face 199B can engage the chamfer 178 in a dovetail-type arrangement to retain the lock arm 129A in the first arm channel 121A by preventing movement of the lock arm 129A in directions non-parallel to axis A while still allowing translation of the lock arm 129A with respect to the body 104 parallel to the axis A. Similarly, the face 201A can engage the chamfer 181 and the face 201B can engage the chamfer 180 in a dovetail-type arrangement to retain the lock arm 129B in the second arm channel 121B by preventing movement of the lock arm 129B in directions non-parallel to axis A while still allowing translations of the lock arm 129B with respect to the body 104 parallel to the axis A. Generally, this arrangement can allow for movement of the lock arms 129A and 129B with respect to the body 104 to allow the lock 106 to secure the anchor 102 to the body 104.

Though the extended tabs 112A and 112B, the lock 106, and the body 104 are discussed above as having chamfered portions to create a dovetail arrangement, other geometries and connection methods can be used to secure the extended tabs 112A and 112B and the lock 106 to the body 104 while enabling relative translation of the extended tabs 112A and 112B and the lock 106 to the body 104.

Figure 9:
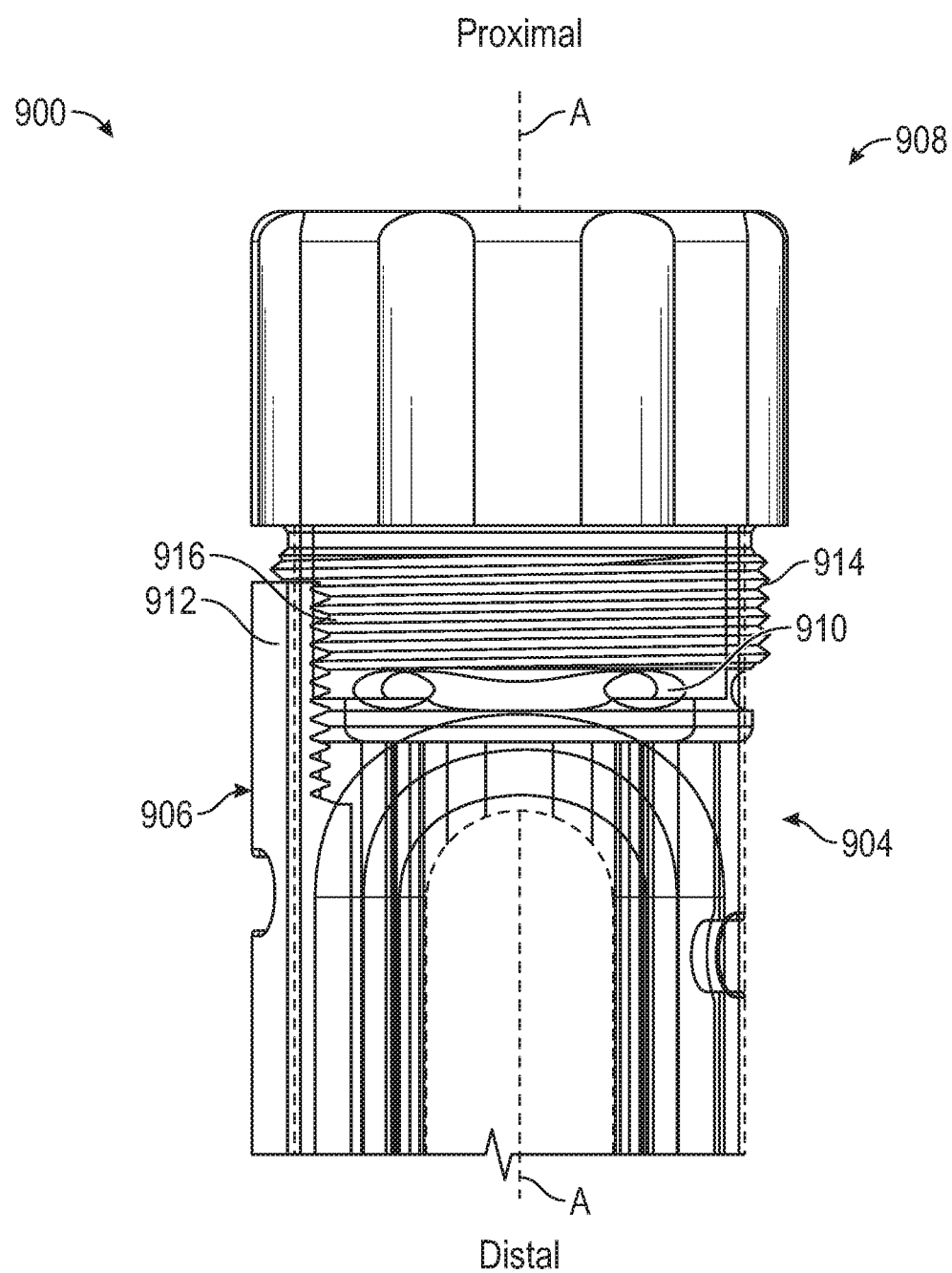
FIG. 9 illustrates a front view of a sleeve assembly with a portion of the sleeve assembly in phantom, in accordance with at least one example of this disclosure.

FIG. 9 illustrates a front view of a sleeve assembly 900 with a portion of the sleeve assembly 900 in phantom, in accordance with at least one example of this disclosure. The sleeve assembly 900 can include a threaded engagement between an actuator and a two-piece lock. Any of the previously discussed sleeve assemblies can be modified to include such an actuator and lock assembly.

The sleeve assembly 900 can include a body 904, a lock 906, and an actuator 908. The body 904 can include a pin slot 910, the actuator 908 can include a pin channel 912 and a male threaded portion 914, and the lock 906 can include a female threaded portion 916. Also shown in FIG. 9 is axis A and orientation indicators Proximal and Distal.

The sleeve assembly 900 can be similar to the sleeve assemblies discussed above, except that the actuator 908 can be secured to the body via a pin passing through the pin slot 910 of the body 904 and the channel 912 of the actuator. The sleeve assembly 900 can also differ in that it can include the male threaded portion 914 on the actuator 908, which can drive the female threaded portion 916 of the lock to translate the lock 906 relative to the body.

Figure 10:
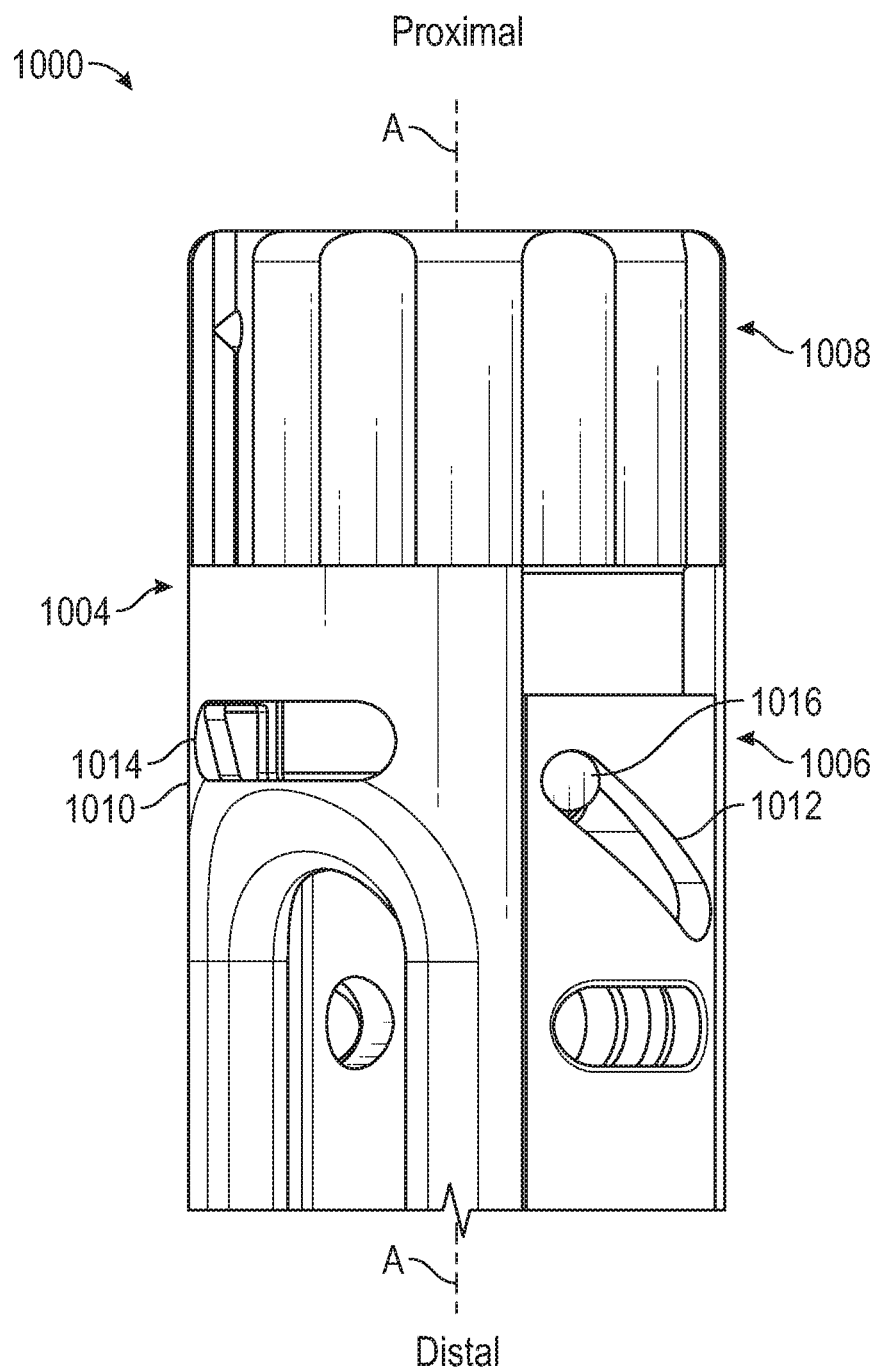
FIG. 10 illustrates a side view of a sleeve assembly, in accordance with at least one example of this disclosure.

FIG. 10 illustrates a side view of a sleeve assembly 1000, in accordance with at least one example of this disclosure. The sleeve assembly 1000 can include a spring boss, and a guide boss to translate a lock. Any of the previously discussed sleeve assemblies can be modified to include such a spring boss and guide boss.

The sleeve assembly 1000 can include a body 1004, a lock 1006, and an actuator 1008. The body 1004 can include spring channel 1010. The lock 1006 can include a guide channel 1012, and the actuator 1008 can include a spring boss 1014, and a guide boss 1016. Also shown in FIG. 10 is axis A and orientation indicators Proximal and Distal.

The sleeve assembly 1000 can be similar to the sleeve assemblies discussed above, except that the actuator 1008 can be secured to the body via the spring boss 1014, which can be disposed within the spring channel 1010 of the body 1004. The spring boss 1014 can rotate within the spring channel 1010 and can limit axial translation of the actuator 1008 with respect to the body 1004.

The sleeve assembly 1000 can also differ in that it can include the guide boss 1016, which can be disposed within the guide channel 1012 of the lock 1006. In some examples, the guide channel 1012 can be a diagonal channel configured to cause axial translation of the lock 1006 when the actuator 1008 is rotated.

In assembly of some examples, the lock 1006 (on both sides) can be aligned with channels of the body 1004. The guide boss 1016 can be inserted into the guide channel 1012. Then, the actuator 1008 and the lock 1006 can be translated distally together until the spring bosses extend radially into the spring channel 1010.

Figure 11A:
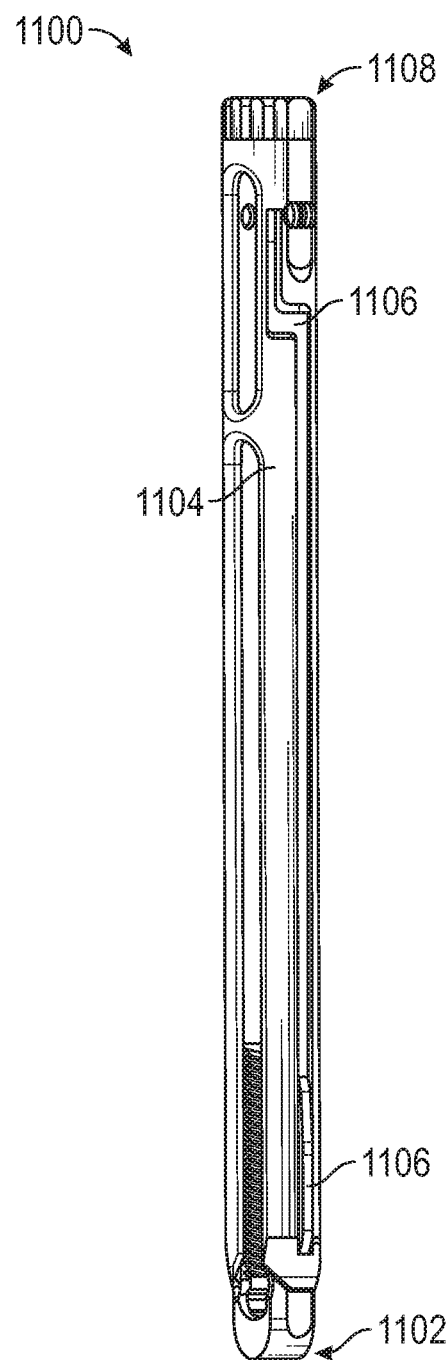
FIG. 11A illustrates a side view of a sleeve assembly, in accordance with at least one example of this disclosure.
Figure 11B:
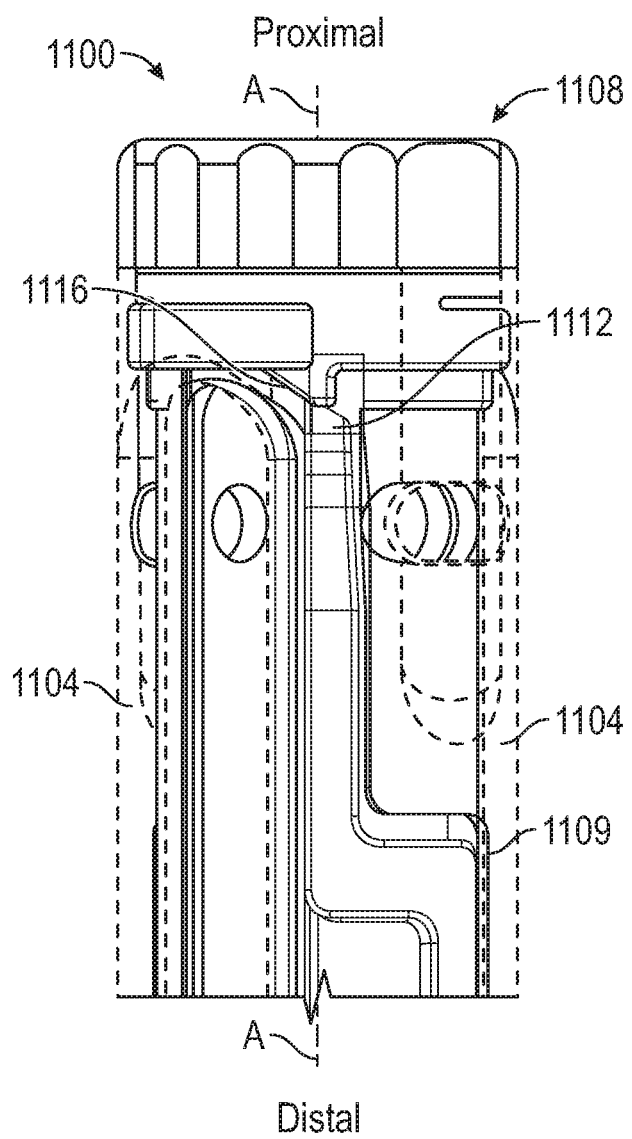
FIG. 11B illustrates a side view of a portion of a sleeve assembly with a portion of the sleeve assembly in phantom, in accordance with at least one example of this disclosure.
Figure 11C:
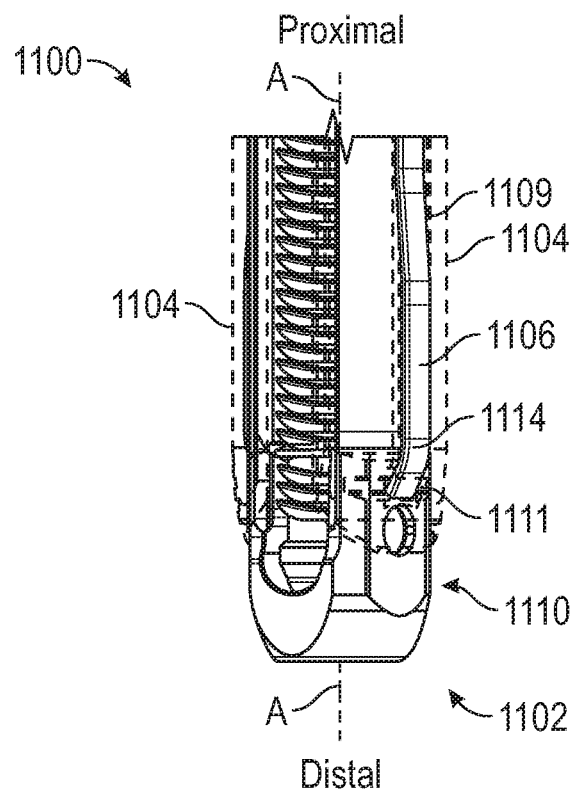
FIG. 11C illustrates a side view of a portion of a sleeve assembly with a portion of the sleeve assembly in phantom, in accordance with at least one example of this disclosure.

FIG. 11A illustrates a side view of a sleeve assembly 1100, in accordance with at least one example of this disclosure. FIG. 11B illustrates a side view of a portion of the sleeve assembly 1100 with a portion of the sleeve assembly 1100 in phantom, in accordance with at least one example of this disclosure. FIG. 11C illustrates a side view of a portion of the sleeve assembly 1100 with a portion of the sleeve assembly 1100 in phantom, in accordance with at least one example of this disclosure. The sleeve assembly 1100 can include a ramp engagement between an actuator and a flexible lock. Any of the previously discussed sleeve assemblies can be modified to include such ramp interface and flexible lock.

The sleeve assembly 1100 can include an anchor 1102, a body 1104, a lock 1106, and an actuator 1108. The body 1104 can include a lock channel 1109. The lock 1106 can include a proximal ramp 1112 and a distal flexible portion 1114. The actuator 1108 can include a guide ramp 1116. The anchor 1102 can include a head 1110 having a notch 1111. Also shown in FIG. 11 is axis A and orientation indicators Proximal and Distal.

The sleeve assembly 1100 can be similar to the sleeve assemblies discussed above, except that the actuator 1108 can engage the proximal ramp 1112 of the lock 1106 such that when the actuator 1008 is rotated, the guide ramp 1116 of the actuator engages the proximal ramp 1112 to cause the lock 1106 to translate parallel to the axis A. The flexible portion 1114 of the lock 1106 can translate within the lock channel 1109 of the body. When the actuator 1108 is moved to the locked position, the flexible portion 1114 can move into the notch 1111 of the head of the anchor 1102 to retain the anchor 1102 within the sleeve assembly 1100.

Figure 12:
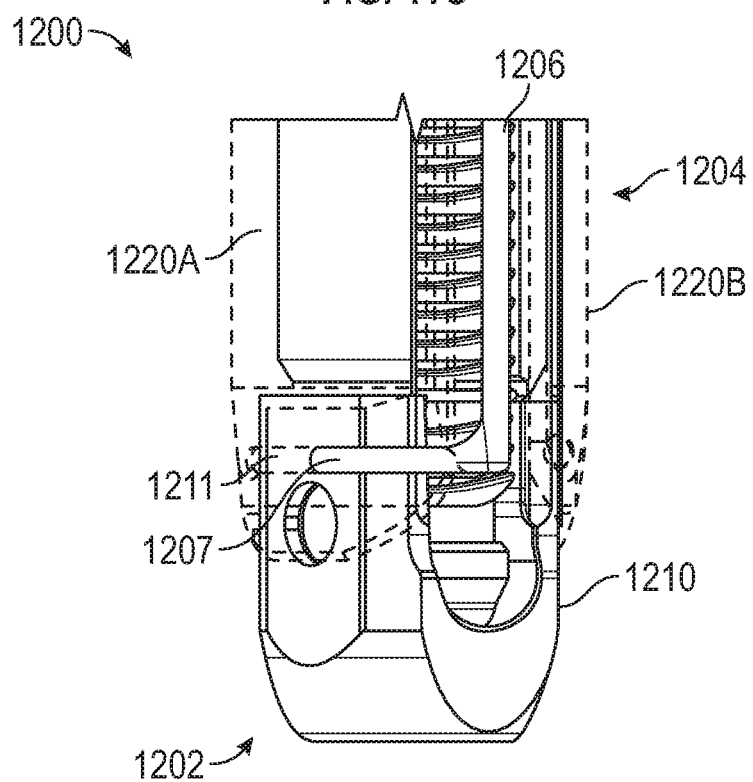
FIG. 12 illustrates a side view of a portion of a sleeve assembly with a portion of the sleeve assembly in phantom, in accordance with at least one example of this disclosure.

FIG. 12 illustrates a side view of a portion of a sleeve assembly 1200 with a portion of the sleeve assembly in phantom, in accordance with at least one example of this disclosure. The sleeve assembly 1200 can include a rotating lock securable to a channel of an anchor. Any of the previously discussed sleeve assemblies can be modified to include such translating lock assembly.

The sleeve assembly 1200 can include an anchor 1202, a body 1204, a lock 1206, and an actuator. The body 1204 can include arms 1220A and 1220B. The lock 1206 can include a ring portion 1207. The anchor 1202 can include a head 1210 having a channel 1211. Also shown in FIG. 12 is axis A and orientation indicators Proximal and Distal.

The sleeve assembly 1200 can be similar to the sleeve assemblies discussed above, except that the lock 1206 can include the ring portion 1207. The lock 1206 can be rotatable by the actuator to rotate the ring portion 1207 into the channel 1211 of the head 1210 to secure the anchor 1202 within the sleeve assembly 1200.

Figure 13:
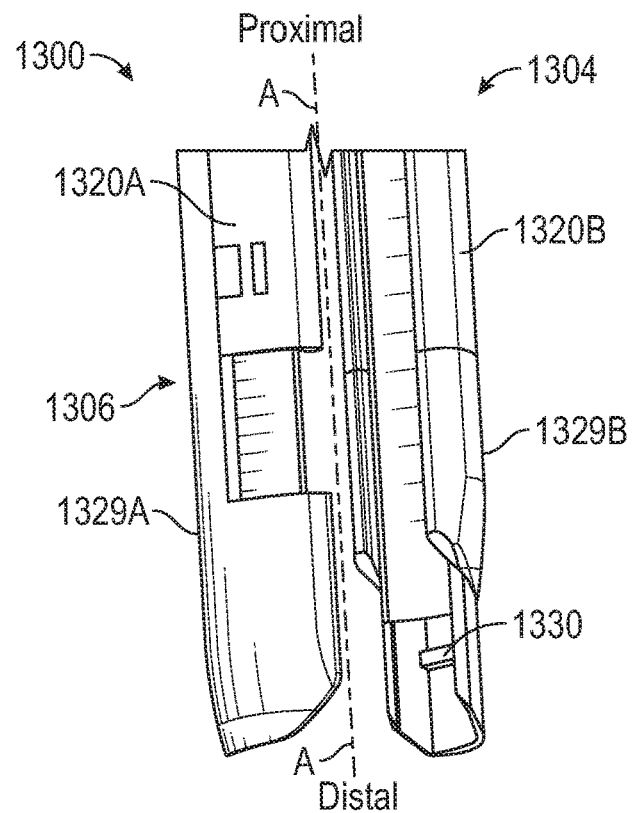
FIG. 13 illustrates an isometric view of a portion of a sleeve assembly, in accordance with at least one example of this disclosure.

FIG. 13 illustrates an isometric view of a portion of a sleeve assembly 1300, in accordance with at least one example of this disclosure. The sleeve assembly 1300 can include translating locks to provide a low number of components. Any of the previously discussed sleeve assemblies can be modified to include such a lock assembly.

The sleeve assembly 1300 can include a body 1304, a lock 1306, and an actuator. The body 1304 can include arms 1320A and 1320B (including a boss 1330). The lock 1306 can include lock arms 1329A and 1329B. Also shown in FIG. 13 is axis A and orientation indicators Proximal and Distal.

The sleeve assembly 1300 can be similar to the sleeve assemblies discussed above, except that the body 1304 can include the boss 1330 and can be flexible at a distal portion of the arm 1320A such that when the lock arm 1329A is moved to a locked position, the boss can engage a channel of an anchor head to retain the anchor within the sleeve assembly. When the lock arms are moved to the unlocked position (as shown with lock arm 1329B), the arms 1320 can extend radially outward to release the anchor. Such an assembly can help reduce the number of total parts.

Figure 14:
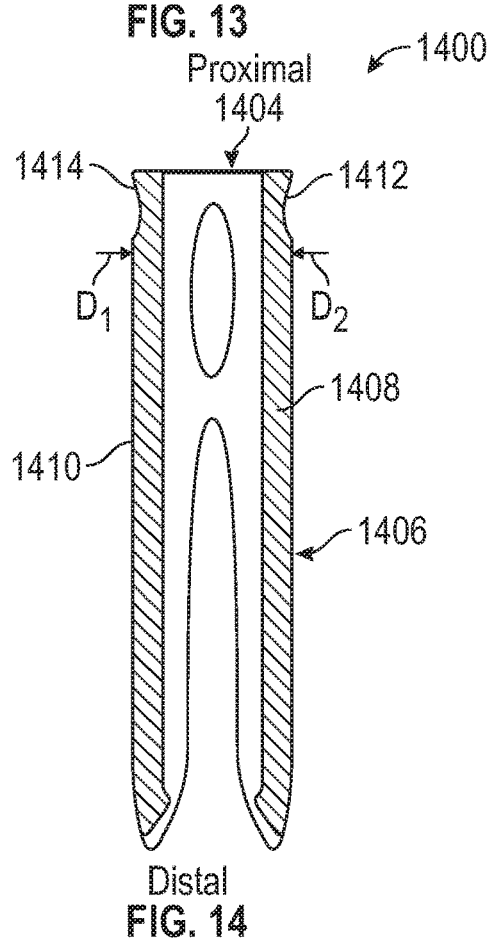
FIG. 14 illustrates a front view of a sleeve assembly, in accordance with at least one example of this disclosure.

FIG. 14 illustrates a front view of a sleeve assembly, in accordance with at least one example of this disclosure. The sleeve assembly 1400 can include a sliding lock without an actuator. Any of the previously discussed sleeve assemblies can be modified to include such a sliding lock.

The sleeve assembly 1400 can include a body 1404 and a lock 1406. The lock 1406 can include lock arms 1408 and 1410, which can respectively include position locks 1412 and 1414. Also shown in FIG. 14 is axis A, directions D1 and D2, and orientation indicators Proximal and Distal.

The sleeve assembly 1400 can be similar to the sleeve assemblies discussed above, except that the lock arms 1408 and 1410 can be prevented from translating with respect to the body 1404 by the position locks 1412 and 1414. A pinching force (shown as directions D1 and D2) can be applied to the position locks 1412 and 1414 to release the lock arms 1408 and 1410, respectively, from the body 1404 to allow translation of the lock arms proximally 1408 and 1410 with respect to the body 1404. Such an assembly can help reduce the number of total parts.

Figure 15A:
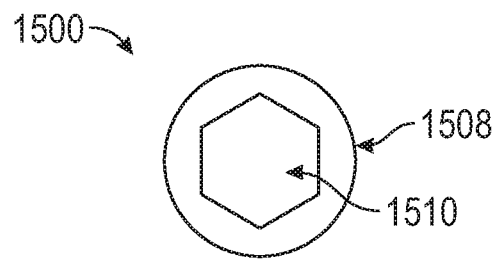
FIG. 15A illustrates a top view of a sleeve assembly, in accordance with at least one example of this disclosure.
Figure 15B:
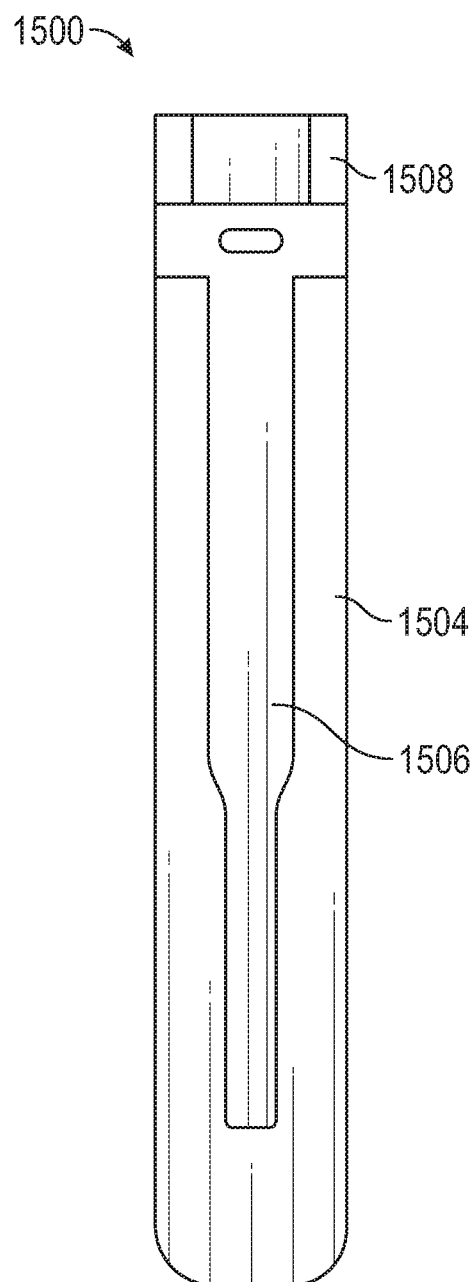
FIG. 15B illustrates a side view of a portion of a sleeve assembly, in accordance with at least one example of this disclosure.

FIG. 15A illustrates a top view of a sleeve assembly 1500, in accordance with at least one example of this disclosure. FIG. 15B illustrates a side view of a portion of the sleeve assembly 1500, in accordance with at least one example of this disclosure. FIGS. 15A and 15B are discussed below concurrently. The sleeve assembly 1500 can include a hex drive to allow a tool to be used to operate the actuator. Any of the previously discussed sleeve assemblies can be modified to include such a hex drive.

The sleeve assembly 1500 can include a body 1504, a lock 1406, and an actuator 1508, which can include a hex drive 1510. The sleeve assembly 1500 can be similar to the sleeve assemblies discussed above, except that the actuator 1508 can include the hex drive 1510 to allow a tool to be used to operate the actuator 1510, which can help save time. In some examples, other drive engagements, such as slot, cross-recess, hexolobular, double hex, or the like.

Figure 16:
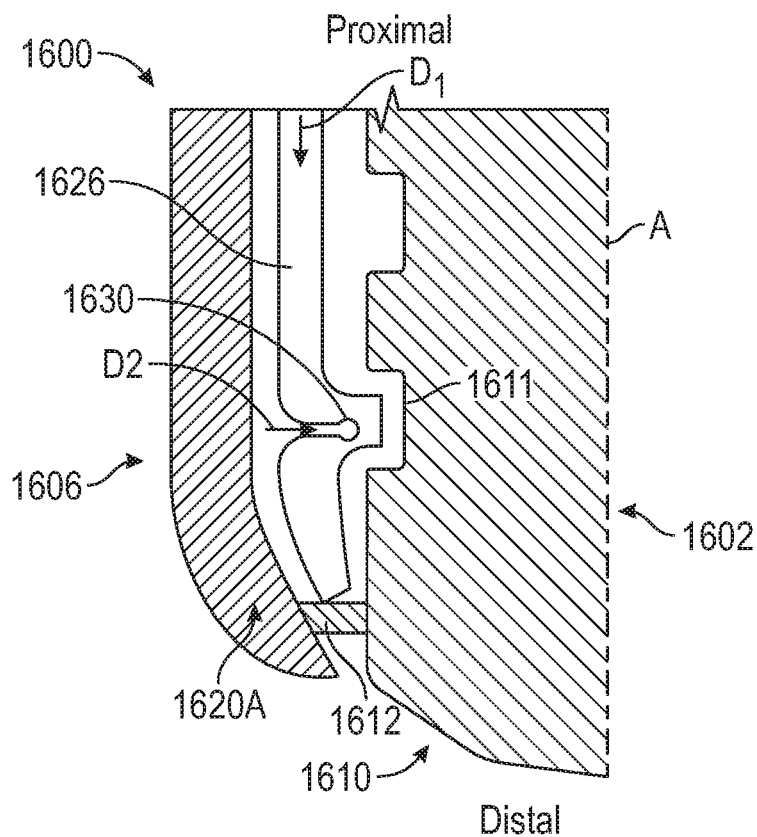
FIG. 16 illustrates a cross-section view of a portion of an anchor and sleeve assembly, in accordance with at least one example of this disclosure.

FIG. 16 illustrates a cross section view of a portion of an anchor 1602 and sleeve assembly 1600, in accordance with at least one example of this disclosure. The sleeve assembly 1600 can include a living hinge lock configured to engage a channel of the anchor. Any of the previously discussed sleeve assemblies can be modified to include such a living hinge lock.

The sleeve assembly 1600 can include a body 1604, a lock 1606, and an actuator. The body 1604 can include a lock arm 1620A and a stop 1612. The lock 1606 can include a spring lock 1626, which can include a living hinge 1630. The anchor 1602 can include a head 1610 having a channel 1611. Also shown in FIG. 16 is axis A, directions D1 and D2, and orientation indicators Proximal and Distal.

The sleeve assembly 1600 can be similar to the sleeve assemblies discussed above, except that the spring lock 1626 can include the living hinge 1630 which can fold or change shape in response to movement in direction D1 and contact between a distal portion of the spring lock 1626 and the stop 1612, resulting in a compressive force. This compressive force can cause the living hinge to compress and move radially inward into the channel 1611 of the head 1610 to retain the anchor 1602 within the sleeve assembly.

Figure 17:
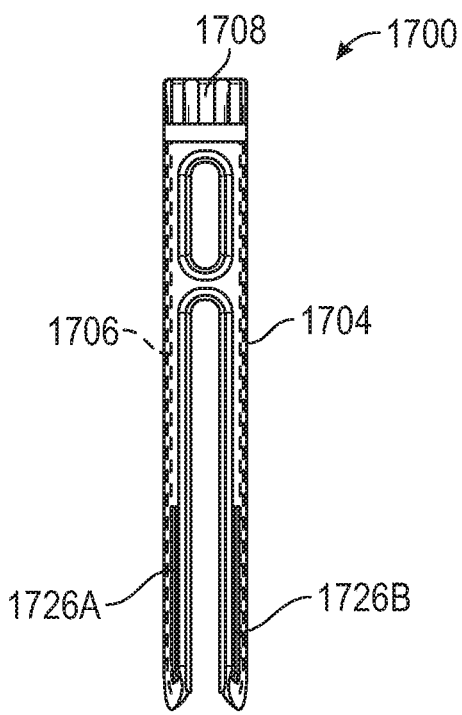
FIG. 17 illustrates a cross-section view of a sleeve assembly, in accordance with at least one example of this disclosure.

FIG. 17 illustrates a cross section view of a sleeve assembly 1700, in accordance with at least one example of this disclosure. The sleeve assembly 1700 can include a lock internal to the body, which can help protect the lock from external forces. Any of the previously discussed sleeve assemblies can be modified to include such an actuator and lock assembly.

The sleeve assembly 1700 can include a body 1704, a lock 1706, an actuator 1708, and spring hooks 1726. The sleeve assembly 1700 can be similar to the sleeve assemblies discussed above, except that the lock 1706 (including the lock arms) can be located within the body 1704 and can be movable therein. Such an internal lock can help reduce external interference of translation of the lock 1706.

Figure 18:
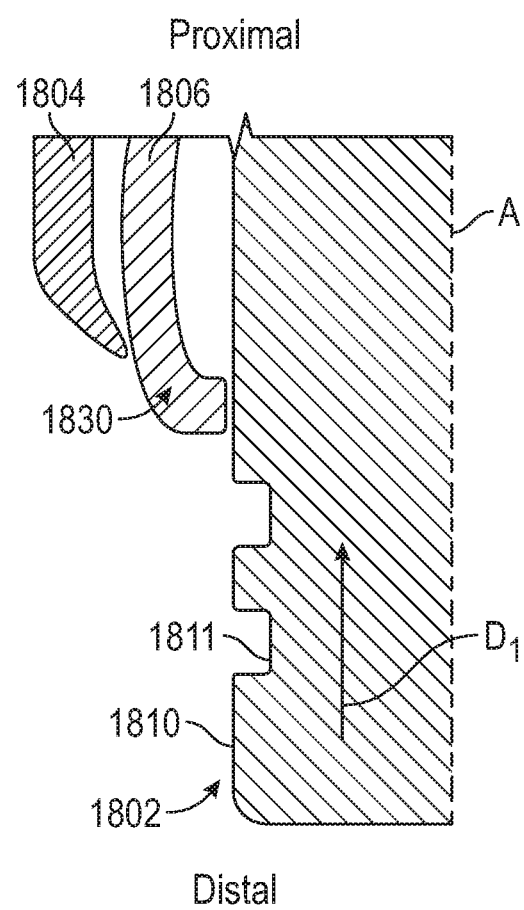
FIG. 18 illustrates a front view of a portion of an anchor and sleeve assembly, in accordance with at least one example of this disclosure.

FIG. 18 illustrates a front view of a portion of an anchor 1802 and sleeve assembly 1800, in accordance with at least one example of this disclosure. The sleeve assembly 1800 can include a lock actuated by insertion of the anchor 1802 into the sleeve. Any of the previously discussed sleeve assemblies can be modified to include such a lock assembly.

The sleeve assembly 1800 can include a body 1804, a lock 1806, and an actuator. The anchor 1802 and include a head 1810 having a channel 1811. The lock can include a projection 1830. FIG. 18 also shows axis A, direction D1, and orientation indicators Proximal and Distal.

The sleeve assembly 1800 can be similar to the sleeve assemblies discussed above, except that the projection 1830 of the lock 1806 can be actuated to move radially inward by insertion of the anchor 1802 into the body 1804, where the anchor 1810 can contact the lock 1806 to cause the projection 1830 to engage the channel 1811 to retain the head 1810 within the sleeve assembly 1800. Such a lock can provide a sleeve without an actuator, which can help reduce the number of parts.

NOTES AND EXAMPLES

The following, non-limiting examples, detail certain aspects of the present subject matter to solve the challenges and provide the benefits discussed herein, among others.

Example 1 is a sleeve adapted to reinforce a bone anchor, the sleeve comprising: a body including a first sleeve arm and a second sleeve arm extending longitudinally along opposing sides of a longitudinal bore open at a distal end of the sleeve, the first and second sleeve arms separated by first and second sleeve slots, the first and second sleeve slots aligned across the longitudinal bore to receive a connecting member therethrough; a lock coupled to the body and releasably securable to a channel of a head of the bone anchor to secure the sleeve to the anchor; and an actuator connected to the body and operable between a locked and an unlocked position, the actuator configured to move the lock to engage the channel when the actuator is moved from the unlocked position to the locked position.

In Example 2, the subject matter of Example 1 optionally includes wherein the longitudinal bore is configured to receive extended tab portions of the head of the anchor therein.

In Example 3, the subject matter of Example 2 optionally includes wherein the first sleeve arm includes a first dovetail slot configured to receive a first extended tab of the anchor therein and wherein the second sleeve arm includes a second dovetail slot configured to receive a second extended tab of the anchor therein.

In Example 4, the subject matter of any one or more of Examples 1-3 optionally include wherein the first sleeve arm includes a first pocket located at a distal portion of the first sleeve arm and the second sleeve arm includes a second pocket located at a distal portion of the second sleeve arm, the lock movable within the first pocket and the second pocket to releasably engage the channel of the head of the anchor.

In Example 5, the subject matter of any one or more of Examples 1-4 optionally include wherein the actuator is a knob coupled to a proximal portion of the body, the knob rotatable to translate the lock relative to the body.

In Example 6, the subject matter of any one or more of Examples 1-5 optionally include a first spring hook secured to a distal portion of the first sleeve arm and a second spring hook secured to a distal portion of the second sleeve arm, the lock engageable with the first spring hook and the second spring hook to force the first spring hook and the second spring hook into the channel when the actuator is in the locked position.

In Example 7, the subject matter of any one or more of Examples 1-6 optionally include wherein the lock includes a first lock arm and a second lock arm, and wherein the first sleeve arm includes a first external slot configured to receive the first lock arm therein and wherein the second sleeve arm includes a second external slot configured to receive the second lock arm therein, the first lock arm and the second lock arm translatable within the first external slot and the second external slot, respectively.

In Example 8, the subject matter of Example 7 optionally includes a first spring hook secured to a distal portion of the first sleeve arm and a second spring hook secured to a distal portion of the second sleeve arm; wherein the first sleeve arm includes a first pocket located at a distal portion of the first sleeve arm and the second sleeve arm includes a second pocket located at a distal portion of the second sleeve arm, the first lock arm movable within the first pocket and the second lock arm movable within the second pocket to respectively engage the first spring hook and the second spring hook to force the first spring hook and the second spring hook into the longitudinal bore to engage the channel of the anchor to retain the anchor within the longitudinal bore when the actuator is in the locked position; and wherein the actuator is a knob coupled to a proximal portion of the body, the knob rotatable to translate the lock arms relative to the body.

In Example 9, the subject matter of Example 8 optionally includes wherein the first spring hook and second spring hook each include a barb extending radially inward to engage the channel of the anchor when the actuator is in the locked position.

In Example 10, the subject matter of Example 9 optionally includes wherein the first spring hook and second spring hook are biased radially outward from the longitudinal bore to limit engagement with the anchor when the actuator is in the unlocked position.

In Example 11, the subject matter of any one or more of Examples 8-10 optionally include wherein the first lock arm and the second lock arm are positioned radially outward of the first spring hook and the second spring hook, respectively, and wherein the first lock arm and second lock arm each include a tapered portion that is tapered radially at a distal portion of each of the first lock arm and the second lock arm.

In Example 12, the subject matter of Example 11 optionally includes wherein the tapered portion of the first lock arm and the tapered portion of the second lock arm are configured to translate into the pocket such that, as the first lock arm and the second lock arm translate distally, the pocket deflects each of the first lock arm and second lock arm, respectively, radially inward to contact the first spring hook and the second spring hook, respectively, to force the first spring hook and the second spring hook into the longitudinal bore to engage the channel of the anchor to retain the anchor within the longitudinal bore.

In Example 13, the subject matter of Example 12 optionally includes wherein the distal tip of each of the first spring hook and the second spring hook include a tip width that is wider than a width of a first hook channel and a second hook channel which respectively connect to the first pocket and the second pocket, to limit radially outward movement of the first spring hook and the second spring hook, respectively, from the first pocket and the second pocket.

In Example 14, the subject matter of any one or more of Examples 8-13 optionally include wherein each of the first spring hook and the second spring hook include a distal tip tapered radially inward to promote radially inward deflection of each of the first spring hook and the second spring hook through contact between each of the first spring hook and the second spring hook and the first pocket and the second pocket, respectively, as the first spring hook and the second spring hook are moved from an unlocked position to a locked position.

In Example 15, the subject matter of any one or more of Examples 8-14 optionally include wherein the cap is threadably couplable to the body and wherein the cap includes a plurality of fingers configured to engage a radially inner portion of the lock to couple the cap to a proximal portion of the lock.

In Example 16, the subject matter of any one or more of Examples 8-15 optionally include wherein the lock includes a proximal bore and the body includes a proximal slot alignable with the proximal bore, each configured to receive a pin therethrough to limit translation of the lock relative to the body.

Example 17 is an implant system for securing an anchor to a bone, the system comprising: an anchor comprising: a head open at a proximal end of the head; a shank extending distally from the head and configured to engage the bone; a first extension extending from a first breakaway portion coupling the first extension to the proximal end of the head; a second extension extending from a second breakaway portion coupling the second extension to the proximal end of the head; and a channel extending around at least a portion of the head, the channel located distal of the first breakaway portion and the second breakaway portion; and a sleeve adapted to reinforce the anchor, the sleeve comprising: a body including a first sleeve arm and a second sleeve arm together extending longitudinally to form a longitudinal bore open at a distal end of the sleeve to receive the head therein, the first and second sleeve arms separated by a first sleeve slot and a second sleeve slot to receive a connecting member therethrough; a lock coupled to the body and releasably engageable with the channel of the head to secure the sleeve to the anchor; and an actuator connected to the body and operable between a locked and an unlocked position, the actuator configured to move the lock to engage the channel when the actuator is moved from the unlocked position to the locked position.

In Example 18, the subject matter of Example 17 optionally includes wherein the first sleeve arm includes a first pocket located at a distal portion of the first sleeve arm and the second sleeve arm includes a second pocket located at a distal portion of the second sleeve arm, the lock movable within the first pocket and the second pocket to releasably engage the channel of the head of the anchor.

In Example 19, the subject matter of Example 18 optionally includes a first spring hook secured to a distal portion of the first sleeve arm and a second spring hook secured to a distal portion of the second sleeve arm, the lock engageable with the first spring hook and the second spring hook to force the first spring hook and the second spring hook into the channel when the actuator is in the locked position.

In Example 20, the subject matter of Example 19 optionally includes wherein the first spring hook and second spring hook each include a barb extending radially inward to engage the channel of the anchor when the actuator is in the locked position, and wherein the first spring hook and second spring hook are biased radially outward from the longitudinal bore to limit engagement with the anchor when the actuator is in the unlocked position.

In Example 21, the apparatuses or methods of any one or any combination of Examples 1-20 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined \with reference to the appended claims, along with the full scope of equivalents to which such claims are entitled.

The invention claimed is:

1. A sleeve, comprising:
   a body including a first sleeve arm and a second sleeve arm extending longitudinally along opposing sides of a longitudinal bore open at a distal end of the sleeve, the first sleeve arm including a first pocket located within a first exterior surface of the first sleeve arm proximate to a distal portion of the first sleeve arm, and the second sleeve arm including a second pocket located within a second exterior surface of the second sleeve arm proximate to a distal portion of the second sleeve arm;
   a lock coupled to the body, the lock movable within the first pocket and the second pocket, wherein the lock includes a proximal bore and the body includes a proximal slot alignable with the proximal bore, each configured to receive a pin therethrough to limit translation of the lock relative to the body; and an actuator connected to the body and operable between a locked position and an unlocked position, the actuator engageable with a proximal portion of the lock, the actuator configured to move the lock within the first pocket and the second pocket when the actuator is moved from the unlocked position to the locked position.

2. The sleeve of claim 1, further comprising:
a first spring hook secured to the distal portion of the first sleeve arm and a second spring hook secured to the distal portion of the second sleeve arm, the lock engageable with the first spring hook and the second spring hook to cause the first spring hook and the second spring hook to engage a channel of a bone anchor when the actuator is in the locked position.

3. The sleeve of claim 2, wherein the first spring hook and second spring hook each include a barb extending radially inward to engage a channel of a bone anchor when the actuator is in the locked position.

4. The sleeve of claim 2, wherein the first spring hook and second spring hook are biased radially outward from the longitudinal bore to provide clearance for insertion of extended tabs of a bone anchor into the sleeve when the actuator is in the unlocked position.

5. The sleeve of claim 2, wherein a distal tip of each of the first spring hook and the second spring hook include a tip width that is wider than a width of a first hook channel and a second hook channel that respectively connect to the first pocket and the second pocket, to limit radially outward movement of the first spring hook and the second spring hook, respectively, from the first pocket and the second pocket.

6. The sleeve of claim 2, wherein each of the first spring hook and the second spring hook include a distal tip tapered radially inward to promote radially inward deflection of each of the first spring hook and the second spring hook through contact between each of the first spring hook and the second spring hook and the first pocket and the second pocket, respectively, as the first spring hook and the second spring hook are moved from an unlocked position to a locked position.

7. The sleeve of claim 2, wherein the lock includes a first lock arm and a second lock arm, and wherein the first lock arm and the second lock arm are translatable within the first pocket and the second pocket, respectively.

8. The sleeve of claim 7, wherein the first lock arm is movable within the first pocket and the second lock arm is movable within the second pocket to respectively engage the first spring hook and the second spring hook to actuate the first spring hook and the second spring hook into the longitudinal bore and cause the first spring hook and the second spring hook to engage a channel of a bone anchor to retain the bone anchor within the longitudinal bore when the actuator is in the locked position,
wherein the actuator is a knob coupled to a proximal portion of the body, and wherein the knob is rotatable to translate the first and second lock arms relative to the body.

9. The sleeve of claim 8, wherein the first lock arm and the second lock arm are positioned radially outward of the first spring hook and the second spring hook, respectively, and wherein the first lock arm and second lock arm each include a tapered portion that is tapered radially at a distal portion of each of the first lock arm and the second lock arm.

10. The sleeve of claim 9, wherein the tapered portion of the first lock arm and the tapered portion of the second lock arm are configured to translate into the corresponding first or second pocket such that, as the first lock arm and the second lock arm translate distally, the first and second pocket deflect each of the first lock arm and second lock arm, respectively, radially inward to contact the first spring hook and the second spring hook, respectively, to actuate the first spring hook and the second spring hook into the longitudinal bore and cause the first spring hook and the second spring hook to engage the channel of the bone anchor to retain the bone anchor within the longitudinal bore.

11. The sleeve of claim 8, wherein the knob is a cap, wherein the cap is threadably couplable to the body via internal threading within the cap that is complementary to external threading on the body, and wherein the cap includes a plurality of fingers configured to engage a radially inner portion of the lock to couple the cap to the proximal portion of the lock.

12. A sleeve, comprising:
a body including a first sleeve arm and a second sleeve arm extending longitudinally along opposing sides of a longitudinal bore open at a distal end of the sleeve, the first sleeve arm including a first pocket located within a first exterior surface of the first sleeve arm proximate to a distal portion of the first sleeve arm, the second sleeve arm including a second pocket located within a second exterior surface of the second sleeve arm proximate to a distal portion of the second sleeve arm;

a lock coupled to the body, the lock movable within the first pocket and the second pocket, the lock positioned exterior to and at least partially surrounding the body; and an actuator connected to the body and operable between a locked position and an unlocked position, wherein the actuator is threadably coupled to the body via internal threading within the actuator that is complementary to external threading on the body, the actuator engageable with a proximal portion of the lock, the actuator configured to move the lock within the first pocket and the second pocket when the actuator is moved from the unlocked position to the locked position.

13. The sleeve of claim 12, further comprising:
a first spring hook secured to the distal portion of the first sleeve arm and a second spring hook secured to the distal portion of the second sleeve arm, the lock engageable with the first spring hook and the second spring hook to cause the first spring hook and the second spring hook to engage a channel of a bone anchor when the actuator is in the locked position.

14. The sleeve of claim 12, wherein the sleeve is releasably securable to a channel of a head of a bone anchor via actuation of the lock to secure the sleeve to the bone anchor, wherein the longitudinal bore is configured to receive extended tab portions of the head of the bone anchor therein, wherein the first sleeve arm includes a first dovetail slot configured to receive a first extended tab of the bone anchor therein, and wherein the second sleeve arm includes a second dovetail slot configured to receive a second extended tab of the bone anchor therein.

15. A sleeve, comprising:
a body including a first sleeve arm and a second sleeve arm extending longitudinally along opposing sides of a longitudinal bore open at a distal end of the sleeve, the first sleeve arm including a first pocket located within a first exterior surface of the first sleeve arm proximate to a distal portion of the first sleeve arm, the second sleeve arm including a second pocket located within a second exterior surface of the second sleeve arm proximate to a distal portion of the second sleeve arm; and an actuator connected to the body and operable between a locked position and an unlocked position, wherein the actuator is threadably coupled to the body via internal threading within the actuator that is complementary to external threading on the body.

16. The sleeve of claim 15, further comprising, a lock coupled to the body, the lock movable within the first pocket and the second pocket, the lock positioned exterior to and at least partially surrounding the body, wherein the sleeve is releasably securable to a channel of a head of a bone anchor via actuation of the lock to secure the sleeve to the bone anchor, and wherein the actuator is configured to move the lock within the first pocket and the second pocket to cause the sleeve to engage the channel when the actuator is moved from the unlocked position to the locked position.

17. The sleeve of claim 16, further comprising:

a first spring hook secured to the distal portion of the first sleeve arm and a second spring hook secured to the distal portion of the second sleeve arm, the lock engageable with the first spring hook and the second spring hook to cause the first spring hook and the second spring hook to engage the channel when the actuator is in the locked position.

18. The sleeve of claim 17, wherein the first spring hook and second spring hook each include a barb extending radially inward to engage a channel of a bone anchor when the actuator is in the locked position, and wherein the first spring hook and second spring hook are biased radially outward from the longitudinal bore to provide clearance for insertion of extended tabs of the bone anchor into the sleeve when the actuator is in the unlocked position.

19. A sleeve, comprising:

a body including a first sleeve arm and a second sleeve arm extending longitudinally along opposing sides of a longitudinal bore open at a distal end of the sleeve, the first sleeve arm including a first pocket located within a first exterior surface of the first sleeve arm proximate to a distal portion of the first sleeve arm, and the second sleeve arm including a second pocket located within a second exterior surface of the second sleeve arm proximate to a distal portion of the second sleeve arm;

a lock coupled to the body, the lock movable within the first pocket and the second pocket; and an actuator connected to the body and operable between a locked position and an unlocked position, the actuator engageable with a proximal portion of the lock, the actuator configured to move the lock within the first pocket and the second pocket when the actuator is moved from the unlocked position to the locked position; and a first spring hook secured to the distal portion of the first sleeve arm and a second spring hook secured to the distal portion of the second sleeve arm, the lock engageable with the first spring hook and the second spring hook to cause the first spring hook and the second spring hook to engage a channel of a bone anchor when the actuator is in the locked position.

* * * * *